US007670829B2

(12) United States Patent
Spagnoli et al.

(10) Patent No.: US 7,670,829 B2
(45) Date of Patent: Mar. 2, 2010

(54) YEAST STRAINS AUTONOMOUSLY PRODUCING STEROIDS

(75) Inventors: Roberto Spagnoli, Paris (FR); Tilman Achstetter, Bremen (DE); Gilles Cauet, Griesheim sur Souffel (FR); Eric Degryse, Crosne (FR); Bruno Dumas, Chateaufort (FR); Denis Pompon, Gif sur Yvette (FR); Jacques Winter, Quincy-Voisins (FR)

(73) Assignee: Aventis Pharma S.A., Antony (FR)

( * ) Notice: Subject to any disclaimer, the term of this patent is extended or adjusted under 35 U.S.C. 154(b) by 815 days.

(21) Appl. No.: 10/470,673

(22) PCT Filed: Jan. 29, 2002

(86) PCT No.: PCT/FR02/00348

§ 371 (c)(1),
(2), (4) Date: Feb. 5, 2004

(87) PCT Pub. No.: WO02/061109

PCT Pub. Date: Aug. 8, 2002

(65) Prior Publication Data

US 2004/0137556 A1   Jul. 15, 2004

(30) Foreign Application Priority Data

Jan. 31, 2001   (FR)   ................................... 01 01294

(51) Int. Cl.
C12N 1/19 (2006.01)
C12N 1/18 (2006.01)
C12P 21/00 (2006.01)
C12P 33/00 (2006.01)
C12P 33/12 (2006.01)
C12P 33/18 (2006.01)
C12P 33/08 (2006.01)
C12N 15/00 (2006.01)
C07H 21/00 (2006.01)

(52) U.S. Cl. ............................... 435/254.21; 435/320.1; 435/69.1; 435/254.2; 435/440; 435/52; 435/56; 435/58; 536/23.2

(58) Field of Classification Search .............. 435/254.2, 435/254.21, 69.1, 440, 52, 56, 58, 320.1; 424/93.51; 536/23.2
See application file for complete search history.

(56) References Cited

U.S. PATENT DOCUMENTS

| 5,137,822 | A |   | 8/1992  | Yabusaki et al. |
| 5,157,135 | A |   | 10/1992 | Tsuji et al. |
| 5,547,868 | A |   | 8/1996  | Miller et al. |
| 5,759,801 | A |   | 6/1998  | Chenivesse et al. |
| 5,965,417 | A |   | 10/1999 | Chenivesse et al. |
| 5,989,881 | A | * | 11/1999 | Chenivesse et al. ......... 435/189 |
| 6,218,139 | B1 |  | 4/2001  | Achstetter et al. |
| 6,503,749 | B2 |  | 1/2003  | Achstetter et al. |
| 7,033,779 | B1 |  | 4/2006  | Cauet et al. |
| 2004/0082025 | A1 | | 4/2004  | Dumas et al. |

FOREIGN PATENT DOCUMENTS

| EP | 0340878 | | 11/1989 |
| EP | 0 360 361 | | 3/1990 |
| EP | 0521780 | | 1/1993 |
| EP | 0574941 | A2 | 12/1993 |
| EP | 0 727 489 | | 8/1996 |
| JP | 2031680 | | 2/1990 |
| JP | 2249488 | | 10/1990 |
| JP | 8242851 | | 9/1996 |
| WO | 99/16886 | | 4/1999 |
| WO | 99/25865 | | 5/1999 |
| WO | WO9940203 | | 8/1999 |
| WO | WO 01/25469 | * | 4/2001 |
| WO | WO02061109 | | 8/2002 |

OTHER PUBLICATIONS

Sousa et al., Microbiology 148(Pt5):1291-1303, 2002.*
Branden et al., Introduction to Protein Structure, Garland Publishing Inc., New York, p. 247, 1991.*
Seffernick et al., J. Bacteriol. 183(8):2405-2410, 2001.*
Witkowski et al., Biochemistry 38:11643-11650, 1999.*
Arreguin De Lorencez Monica et al., Regulation Of Gluconeogenic Enzymes During The Cell Cycle Of *Saccharomyces cerevisiae* Growing In A Chemostat, Journal Of General Microbiology, (1987), vol. 133, pp. 2517-2522.
Bonneaud Nathalie et al., A Family Of Low And High Copy Replicative, Integrative And Single-Stranded *S. cerevisiae/E. coli* Shuttle Vectors, Yeast, (1991), vol. 7, pp. 609-615.
Burgers Peter M. J. et al., Transformation Of Yeast Spheroplasts Without Cell Fusion, Analytical Biochemistry, (1987), vol. 163, pp. 391-397.
Cauet Gilles et al., CYP11A1 Stimulates The Hydroxylase Activity Of CYP11B1 In Mitochondria Of Recombinant Yeast In Vivo And In Vitro, European Journal of Biochemistry (2001) 268 pp. 4054-4062.
Cauet Gilles et al., Pregnenolone Esterification in *Saccharomyces cerevisiae*: A Potential Detoxification Mechanism, European Journal Of Biochemistry, (1999), vol. 261, pp. 317-324.
Chua Streamson C. et al., Cloning Of cDNA Encoding Steroid 11 Beta-Hydroxylase (P450c11), Proc. Natl. Acad. Sci. USA, (1987), vol. 84, pp. 7193-7197.
Degryse E et al., Pregnenolone Metabolized To 17 Gamma Hydroxyprogesterone In Yeast: Biochemical Analysis Of A Metabolic Pathway, Journal Of Steroid Biochemistry & Molecular Biology (1999) pp. 239-246.
Degryse Eric et al., In Vivo Cloning By Homologous Recombination In Yeast Using A Two-Plasmid-Based System, Yeast, (1995), vol. 11, pp. 629-640.

(Continued)

*Primary Examiner*—Delia M Ramirez

(57) ABSTRACT

The present invention relates to genetically modified yeast strains autonomously producing, from a simple carbon source, steroids. The invention also relates to a method for producing steroids from such yeast strains.

23 Claims, 5 Drawing Sheets

OTHER PUBLICATIONS

Degryse Eric, In Vivo Intermolecular Recombination In *Escherichia coli*: Application To Plasmid Constructions, Gene, (1996), vol. 170, pp. 45-50.

Dumas Bruno et al., 11 Beta-Hydroxylase Activity In Recombinant Yeast Mitochondria In Vivo Conversion Of 11-Deoxycortisol To Hydrocortisone, European Journal of Biochemistry (1996) 238 pp. 495-504.

Duport Catherine et al., Self-Sufficient Biosynthesis Of Pregnolone And Progesterone In Engineered Yeast, Nature Biotechnology (1998) 16 pp. 186-189.

Hu Meng-Chun et al., Expression Of Human 21-Hydroxylase (P45Oc21) In Bacterial And Mammalian Cells: A System To Characterize Normal And Mutant Enzymes, Molecular Endocrinology, (1990), vol. 4, pp. 893-898.

Kawamoto Takeshi et al., Cloning Of cDNA And Genomic DNA For Human Cytochrome P-45011 Beta, FEBS, 1990), vol. 269, No. 2, pp. 345-349.

Kuronen Pirjo et al., Reversed-Phase Liquid Chromatographic Separation And Simultaneous Profiling Of Steroidal Glycoalkaloids And Their Aglycones, Journal Of Chromatography A, (1999), vol. 863, pp. 25-35.

Lacour Thierry et al., Characterization Of Recombinant Adrendoxin Reductase Homologue (Arhlp) From Yeast, The Journal Of Biological Chemistry (1993) 273 pp. 23984-23992.

Lathe R. et al., Plasmid And Bacteriophage Vectors For Excision Of Intact Inserts, Gene, (1987), vol. 57, pp. 193-201.

Lecain Eric et al., Cloning by Metabolic Interference In Yeast And Enzymatic Characterization Of *Arabidopsis thaliana* Sterol Delta 7-Reductase, The Journal Of Biological Chemistry, (1996), vol. 271, No. 18, pp. 10866-10873.

Li Jie et al., Adrenodoxin Reductase Homolog (Arhlp) Of Yeast Mitochondria Required For Iron Homeostasis, The Journal Of Biological Chemistry (2001) pp. 1503-1509.

Nacken Valerie et al., Probing The Limits Of Expression Levels By Varying Promoter Strength And Plasmid Copy Number In *Saccharomyces cerevisiae*, Gene, (1996), vol. 125, pp. 253-260.

Parent Stephan A. et al., Vector Systems For The Expression, Analysis And Cloning Of DNA Sequences In *S. cerevisiae*, Yeast, (1985), vol. 1, pp. 83-138.

Riesenberg D. et al., High-Cell-Density Cultivation Of Microorganisms, Appl Microbiol Biotechnology, (1999), vol. 51, pp. 422-430.

Skaggs B.A. et al., Cloning And Characterization Of The *Saccharomyces cervisiae* C-22 Sterol Desaturase Gene, Encoding A Second Cytochrome P-450 Involved In Ergosterol Biosynthesis, Gene (1996) pp. 105-109.

Szczebara Florence Menard et al., Total Biosynthesis Of Hydrocortisone From A Simple Carbon Source In Yeast, Nature Biotechnology (2003) 21 pp. 143-149.

Thierry Agnes et al., The Complete Sequence Of THe 8.2kb Segment Left Of MAT On Chromosome III Reveals Five ORFs, Including A Gene For A Yeast Ribokinase, Yeast, (1990), vol. 6, pp. 521-534.

Urban Philippe et al., Characterization Of Recombinant Plant Cinnamate 4-Hydroxylase Produced In Yeast: Kinetic And Spectral Properties Of The Major Plant P450 Of The Phenylpropanoid Pathway, European Journal Of Biochemistry, (1994), vol. 222, pp. 843-850.

Valvo L. et al., General High-Performance Liquid Chromatographic Procedures For The Rapid Screening Of Natural And Synthetic Corticosteroids, Journal Of Pharmaceutical & Biomedical Analysis, (1994), vol. 12, No. 6, pp. 805-810.

Wu Du-An et al., Expression And Functional Study Of Wild-Type And Mutant Human Cytochrome P450c21 In *Saccharomyces cerevisiae*, DNA And Cell Biology, (1991), vol. 10, No. 3, pp. 201-209.

Yang Hongyuan et al., Sterol Esterificatio In Yeast: A Two-Gene Process, Science (1996) 272 pp. 1353-1356.

Yanisch-Perron Celeste et al., Improved M13 Phage Cloning Vectors And Host Strains: Nucleotide Sequences Of The M13mpl8 And pUC19 Vectors, Gene, (1985), vol. 33, No. 1, pp. 103-119.

Zhao Hui-Fen et al., Molecular Cloning, cDNA Structure And Predicted Amino Acid Sequence Of Bovine 3Beta-Hydroxy-5-Ene Steroid Dehydrogenase/Gamma5—Gamma4 Isomerase, FEB, (1989), vol. 259, No. 1, pp. 153-157.

Alani et al., A Method for Gene Disruption That allows Repeated Use of URA3 Selection in the Construction of Multiny Disrupted yeast Strains, Genetics, vol. 116, Aug. 1987, pp. 541-545.

Altschul et al., Basic Local Alignment Search Tool, J. Mol. Biol. vol. 215, 1980, pp. 403-410.

Ashman et al., Cloning and Disruption of the Yeast C-8 Sterol Isomerase Gene. Lipis, vol. 26, No. 8, 1991, pp. 628-632.

Bach et al., Evidence for transcriptional regulation of orotidine-5'-phosphte decarboxylase in yeast by hybridization of mRNA to the yeast structural gene cloned in Escherichia coli, PNAS, vol. 76, No. 1, Jan. 1979, pp. 386-390.

Bard et al., Steroi Mutants of Saccaromyces cerevisiae: Chromatographic Analyses, Lipids, vol. 12(8), 1977, pp. 645-654.

Baudin et al., A simple and efficient method for direct gene deletion in Saccharcymces cerevisiae, Nucleic Acids Research, vol. 1993, No. 14, pp. 3329-3330.

Clejan et al., Rates of Amphotencin B and Filipin Association with Sterois, J. of Bio.Chem., vol. 260, No. 5, Mar. 10, 1985, pp. 2884-2889.

Corey et al., Isolation of an Arabidopsis thaliana gene encoding cycloartenol synthase by functional expression in a yeast mutant lacking lanosterol synthase by the use of a chromatographic screen, PNAS, vol. 90, Dec. 1993, pp. 11628-11632.

Delourme et al., Cloning of an Arabidopsis thaliana cDNA coding for farnesyl diphosphate synthase by functional complementation in yeast (Abstract only), Plant Mol Bio. vol. 26, No. 6, Dec. 1994, pp. 1867-1873.

Dumas et al. Expression of a bovine P450c17 cDNA in the yeast Saccharomyces cerevisias, int'l Conference, Ed. M.C. Lachner, John Libbey Eurotext, Paris, 1994, pp. 427-430.

Fitzky et al., Mutations in the 7-sterol reductase gene in patients with the Smith-Lemli-Optiz syndrome, PNAS, vol. 95, Jul. 1998, pp. 8181-8186.

Fuji et al., Acetate Ester Production by Sacharomyces cerevisiae Lacking the ATF1 Gene Encoding the Alcohol Acetyltransferase, J. of Ferm. and Bioengineering, vol. 81, No. 6, 1996, pp. 538-542.

Gobeil et al., Intracellular Sequestration of Hetero-oligomers Formed by Wild-Type and Glaucoma-Causing Myocilin Mutants, IOVS, vol. 45, No. 10, Oct. 2004. pp. 3560-3567.

Johanson et al., :Strain engineering for stereoselective bioreduction of dicarbonyl compounds by yeast reductases, FEMS Yeast Research, vol. 5, 2005, pp. 513-525.

Johnson, Metabolic Interference and the +- Heterozygoet., A Hypothetical Form of Simple Inheritance Which is Neither Dominant nor Recessive, Am. J. Hum Genet. vol. 32, 1980, pp. 374-386.

Kawata et al. Microsomal Enzymes of Cholesterol Biosynthesis from Lanosterol, J. of Biol., Chem., vol. 260, No. 11, Jun. 10, 1985, pp. 6609-6617.

Kissel, Molecular cloning and expression of cDNA for rat pancreatic cholesterol esterase, Biochimica et biphysica acta 1006, 1989, pp. 227-236.

Kuromori et al., Cloning of cDNAs form Arabidopsis thaliana that encode putative protein phosphatase 2C and a human Dr1-like protein by transformation of a fission yeast mutant, Nucleic Acids Research, vol. 2, No. 24, 1994, pp. 5296-5301

Lorenz et al., Cloning Sequencing, and Disruption of the Gene Encoding Sterol C-14 reductase in Sacharomyces cerevisiae, DNA and Cell Biology, vol. 11, No. 9, 1992, pp. 685-692.

Magdolen et al., Transcriptional control by galactose of a yeast gene encoding a protien homologous to mammalian aldo/keto reductase, Gene, vol. 90, 1990, pp. 105-114.

Marcireau et al., In Vivo Effects of Fenpropimorph on the Yeast Saccharomyces cerevisiae and Determination of the Moelcular Basis of the Antifungal Property, Antimicrobial Agents and Chemotheray, vol. 34, No. 6, Jun. 1990, pp. 989-993.

Minet et al., Cimpletionof Saccharomyes crevisiae autotrophic mutants by Arabidopsis thaliana cDNAs, The Plant Journal, vol. 2, No. 3, 1992, pp. 417-422.

Misoga et al., Accession No. Q12458, Nov. 1, 1997.

Moebius et al., Molecular cloning and expression of the human 7-Sterol Reductase, PNAS, vol. 95, Feb. 1998, pp. 1899-1902.

Nagasawa et al., Cloning and Nucleotide Sequence of the Alcohol Acetyltransferase II Gene (ATF2) from Saccharomyces cerevisiae Kyokai No. 7., Biosci. Biotechnol. Biochem, vol. 62, No. 10, 1998, pp. 1852-1857.

Newman et al., Genes Galor: A Summary of Methods for Accessing Results form Large-Scale Partial Sequencing of Anonymous Arabidopsis cDNA Clones, Plant Physiol. vol. 106, 1994, pp. 1241-1255.

Norbeck et al., Metabolic and Regulatory Changes Associated with Growth of Sacharomyces cerevisiae in 1,4 m NaC1, J. of Biol. Chem., vol. 272, No. 9, Feb. 28, 1997, pp. 5544-5554.

Oechsner et al., A nuclear yeast gene (GCY) encodes a polypeptide with high homology toa vertebrate eye lens protein, FEB vol. 238, No. 1, Sep. 1988, pp. 123-128.

Opitz et al., Cholesterol Metabolism in the RSH/Smith-Lemli-Optiz Syndrome: Summary of an NICHD Conference, Am. J of Medical Genetics, vol. 50, 1994, pp. 326-338.

Riou, Isolation and characterization of cDNA encoding Arabidopsis thaliana mevalonate kinase by genetic complementation in yeast, Gene, vol. 148, 1994, pp. 293-297.

Sakaki et al., Exprssion of Bovine Cytochrome P450c21 and Its fused Enzymes with Yeast NADPH-Cytochrome P450 Reductase in Saccharomyces cerevisiae, DNA and Cell Biology, vol. 9, No. 9, 1990, pp. 603-614.

Sakaki et al., Expression of Bovine Cytochrome P450c17 cDNA in Saccharomyces cerevisiae, DNA, vol. 8, No. 6, pp. 409-418.

Sakaki et al., Progesterone metabolism in recombinant yeast simultaneously expressing bove cytochromes P50c17 (CYP17A1) and P450c21 (CYP21B1) and yeast NADPH-P450 oxidoreductase, Pharmacogenstics, vol. 1, 1991, pp. 86-93.

Servouse et al, Isolation and characterization of yeast Mutants Blocked in Mevalonic Acid Formation, Biochem & Biophys. Res. Comm. vol. 123, No. 2, Sep. 17, 1984.

Servouse et al., Regulation of early enzymes of ergosterol biosynthesis in Saccharomyces cerevisias, Biochem, J. vol. 241, 1986, pp. 541-547.

Taketani et al., Characterization of Sterol-Ester Synthetase in Saccharomyces Cerevisiae, Biochimia et Biophysica Acta, vol. 575, 1979, pp. 148-155.

Urban et al., Cloning Yeast Expression, and characterization of the coupling of Two distantly related Arabidopsos thaliana NADPH-Cylochrome P450 Reductases with P450 CYP73A5, J. of Biol. Chem., vol 272, No. 31, Aug. 1, 1997, pp. 19176-19196.

Wada et al., Expression of Functional Bovine Cholesterol Side chain Cleavage cytochrome P450 (P450scc) in Escherichia coli, Arch. of Biochem & Biophysics, vol. 290, No. 2, Nov. 1, 1991, pp. 376-380.

Winston et al., Construction of a Set of Convenient Saccharomyces ceevisiae Strains that are Isogenic to S288C Yeast, vol. 11, 1995, pp. 53-55.

Winzeler et al., Functional Characterizaiton of the S, cerevisiae Genome by Gene Deletion and Parallel Analysis, Science, vol. 285, Aug. 6, 1999, pp. 901-906.

Xu et al., Reproducing Abnormal Cholesterol Biosynthesis as Seen in the Smith-Limil-Optiz Syndrome by inhibiting the Conversion of 7-Dehydrocholesterol to Cholesterol in Rats, J. of Clinical Investigation, vol. 95, Jan. 1995, pp. 76-81.

Zweytick et al., Contribution of Are1p and Are2p to steryl ester synthesis in the yeast Saccharomyces cerevisiae, Europeon Journal of Biochemistry, vol. 267, Issue 4, 2000, pp. 1075-1082.

Ritter et al., Purification and Characterization of a Naturally Occurring Activator of cholesterol Biosynthesis From 5. 7-Cholestadienol and Other Precursors, Biochem & Biophys Res. Comm., vol. 38, No. 5, 1970, pp. 921-929.

Taton et al., Identification of 5,7-Sterol-7-Reductase In Higher Plant Microsomes, Biochem & Biophysical Res. Comm., vol. 181, No. 1, 1991, pp. 465-473.

Dempsey, M.E., sterol 50Dehydrogenase and 7-Reductase, Methods in Enzymology, vol. 15, 1969 pp. 501-504.

Andersson et al., Cloning, Structure and Expression of the Mitochondrial Cytochrome P-450 Steroi 26-Hydorxylse, a Bile Acid Biosynthetic Enzyme, J. of Biol. Chem. vol. 264, No. 14, May 15, 1989, pp. 8222-8229.

Saunders-Singer, Ascus Dissection, Methods in Molecular Biology, vol. 53, Yeast Protocols, pp. 59-67.

Wach et al., 5 PCR-Based Gene Targeting in Saccharomyces cerevisiae, Methods in Microbiology, vol. 26, 1998, Chapter 6.

* cited by examiner

SEQUENCE LISTING

```
<160> NUMBER OF SEQ ID NOS: 49

<210> SEQ ID NO 1
<211> LENGTH: 32
<212> TYPE: DNA
<213> ORGANISM: Artificial sequence
<220> FEATURE:
<223> OTHER INFORMATION: Oligonucleotide OTG11314 to amplify the 5'
      portion of YPR1

<400> SEQUENCE: 1
tacgctcgag acgttggtgt cattgatatt ca                                    32

<210> SEQ ID NO 2
<211> LENGTH: 21
<212> TYPE: DNA
<213> ORGANISM: Artificial sequence
<220> FEATURE:
<223> OTHER INFORMATION: Oligonucleotide OTG11315 to amplify the 5'
      portion of YPR1
```

-continued

<400> SEQUENCE: 2
cttcattcaa atagatagcc g                                         21

<210> SEQ ID NO 3
<211> LENGTH: 22
<212> TYPE: DNA
<213> ORGANISM: Artificial sequence
<220> FEATURE:
<223> OTHER INFORMATION: Oligonucleotide OTG11316 to amplify the 3'
      portion of YPR1

<400> SEQUENCE: 3
tatggctaaa aagcacggcg tt                                        22

<210> SEQ ID NO 4
<211> LENGTH: 31
<212> TYPE: DNA
<213> ORGANISM: Artificial sequence
<220> FEATURE:
<223> OTHER INFORMATION: Oligonucleotide OTG11317 to amplify the 3'
      portion of YPR1

<400> SEQUENCE: 4
cgatctcgag tttctcgttg ttcaggtact g                              31

<210> SEQ ID NO 5
<211> LENGTH: 65
<212> TYPE: DNA
<213> ORGANISM: Artificial sequence
<220> FEATURE:
<223> OTHER INFORMATION: Oligonucleotide OTG11463 to amplify URA3
      flanked by YPR1

<400> SEQUENCE: 5
cggctatcta tttgaatgaa gatcgatttt caattcaatt catcattttt ttattctttt    60
ttttg                                                               65

<210> SEQ ID NO 6
<211> LENGTH: 58
<212> TYPE: DNA
<213> ORGANISM: Artificial sequence
<220> FEATURE:
<223> OTHER INFORMATION: Oligonucleotide OTG11464 to amplify URA3
      flanked by YPR1

<400> SEQUENCE: 6
aacgccgtgc tttttagcca taagcttggg taataactga tataattaaa tagtactc     58

<210> SEQ ID NO 7
<211> LENGTH: 40
<212> TYPE: DNA
<213> ORGANISM: Artificial sequence
<220> FEATURE:
<223> OTHER INFORMATION: Oligonucleotide OTG7410 to amplify the human
      P450c21 cDNA

<400> SEQUENCE: 7
ggaattccgt cgacaaaaat gctgctcctg ggcctgctgc                     40

<210> SEQ ID NO 8
<211> LENGTH: 29
<212> TYPE: DNA
<213> ORGANISM: Artificial sequence
<220> FEATURE:
<223> OTHER INFORMATION: Oligonucleotide OTG5927 to amplify the human P450c21 cDNA

<400> SEQUENCE: 8
cctcaatggt cctcttggag ttcagcacc                                    29

<210> SEQ ID NO 9
<211> LENGTH: 32
<212> TYPE: DNA
<213> ORGANISM: Artificial sequence
<220> FEATURE:
<223> OTHER INFORMATION: Environment surrounding the translation
      initiation codon ATG of P450c21

<400> SEQUENCE: 9
gtcgacaaaa atgctgctcc tgggcctgct gc                                32

<210> SEQ ID NO 10
<211> LENGTH: 23
<212> TYPE: DNA
<213> ORGANISM: Artificial sequence
<220> FEATURE:
<223> OTHER INFORMATION: Oligonucleotide OTG11844

<400> SEQUENCE: 10
tttgctcgag gttacagaag ggc                                          23

<210> SEQ ID NO 11
<211> LENGTH: 24
<212> TYPE: DNA
<213> ORGANISM: Artificial sequence
<220> FEATURE:
<223> OTHER INFORMATION: Oligonucleotide OTG11845

<400> SEQUENCE: 11
gattctcgag caattggctg acta                                         24

<210> SEQ ID NO 12
<211> LENGTH: 14
<212> TYPE: DNA
<213> ORGANISM: Artificial sequence
<220> FEATURE:
<223> OTHER INFORMATION: Oligonucleotide OTG11975

<400> SEQUENCE: 12
aaatcgataa catg                                                    14

<210> SEQ ID NO 13
<211> LENGTH: 14
<212> TYPE: DNA
<213> ORGANISM: Artificial sequence
<220> FEATURE:
<223> OTHER INFORMATION: Oligonucleotide OTG11976

<400> SEQUENCE: 13
ttatcgattt catg                                                    14

<210> SEQ ID NO 14
<211> LENGTH: 30
<212> TYPE: DNA
<213> ORGANISM: Artificial sequence
<220> FEATURE:
<223> OTHER INFORMATION: Oligonucleotide OTG11981

<400> SEQUENCE: 14
attgatatcg ataaaaagca cggcgttgag                                   30

<210> SEQ ID NO 15
<211> LENGTH: 26
<212> TYPE: DNA
<213> ORGANISM: Artificial sequence
<220> FEATURE:
<223> OTHER INFORMATION: Oligonucleotide OTG11982

<400> SEQUENCE: 15
tctcggaatt caggtactgc agccag                                          26

<210> SEQ ID NO 16
<211> LENGTH: 30
<212> TYPE: DNA
<213> ORGANISM: Artificial sequence
<220> FEATURE:
<223> OTHER INFORMATION: Oligonucleotide OTG11980

<400> SEQUENCE: 16
caactaagct tcattcaaat agatagccgc                                      30

<210> SEQ ID NO 17
<211> LENGTH: 50
<212> TYPE: DNA
<213> ORGANISM: Artificial sequence
<220> FEATURE:
<223> OTHER INFORMATION: Oligonucleotide OTG11285

<400> SEQUENCE: 17
gattcggtaa tctccgaaca ggtaccaatt atatcagtta ttacccggga              50

<210> SEQ ID NO 18
<211> LENGTH: 19
<212> TYPE: DNA
<213> ORGANISM: Artificial sequence
<220> FEATURE:
<223> OTHER INFORMATION: Oligonucleotide OTG11286

<400> SEQUENCE: 18
agccatcttc aaagcggtt                                                  19

<210> SEQ ID NO 19
<211> LENGTH: 22
<212> TYPE: DNA
<213> ORGANISM: Artificial sequence
<220> FEATURE:
<223> OTHER INFORMATION: Oligonucleotide OTG11287

<400> SEQUENCE: 19
ccgatcgaat caaaacgaac ag                                              22

<210> SEQ ID NO 20
<211> LENGTH: 20
<212> TYPE: DNA
<213> ORGANISM: Artificial sequence
<220> FEATURE:
<223> OTHER INFORMATION: Oligonucleotide OTG11289

<400> SEQUENCE: 20
tctaatcagc tagtaagaac                                                 20

<210> SEQ ID NO 21
<211> LENGTH: 67
<212> TYPE: DNA
<213> ORGANISM: Artificial sequence
<220> FEATURE:
<223> OTHER INFORMATION: Oligonucleotide OTG11305

-continued

<400> SEQUENCE: 21
aaccgctttg aaagatggct atcgatttc aattcaattc atcatttttt ttttattctt    60
tttttg    67

<210> SEQ ID NO 22
<211> LENGTH: 60
<212> TYPE: DNA
<213> ORGANISM: Artificial sequence
<220> FEATURE:
<223> OTHER INFORMATION: Oligonucleotide OTG11306

<400> SEQUENCE: 22
ctgttcgttt tgattcgatc gggaagcttg ggtaataact gatataatta aattgaactc    60

<210> SEQ ID NO 23
<211> LENGTH: 138
<212> TYPE: PRT
<213> ORGANISM: Artificial sequence
<220> FEATURE:
<223> OTHER INFORMATION: N-Terminal Sequence of the protein constructed
      for the expression of P450c11

<400> SEQUENCE: 23

Met Leu Ser Arg Ala Ile Phe Arg Asn Pro Val Ile Asn Arg Thr Leu
 1               5                  10                  15

Leu Arg Ala Arg Pro Gly Ala Tyr His Ala Thr Arg Leu Thr Lys Asn
            20                  25                  30

Thr Phe Ile Gln Ser Arg Lys Tyr Gly Thr Arg Gly Ala Ala Ala Pro
        35                  40                  45

Lys Ala Val Leu Pro Phe Glu Ala Met Pro Arg Cys Pro Gly Asn Lys
    50                  55                  60

Trp Met Arg Met Leu Gln Ile Trp Arg Glu Gln Gly Tyr Glu Asp Leu
65                  70                  75                  80

His Leu Glu Val His Gln Thr Phe Gln Glu Leu Gly Pro Ile Phe Arg
                85                  90                  95

Tyr Asp Leu Gly Gly Ala Gly Met Val Cys Val Met Leu Pro Glu Asp
            100                 105                 110

Val Glu Lys Leu Gln Gln Val Asp Ser Leu His Pro His Arg Met Ser
        115                 120                 125

Leu Glu Pro Trp Val Ala Tyr Arg Gln His
    130                 135

<210> SEQ ID NO 24
<211> LENGTH: 37
<212> TYPE: DNA
<213> ORGANISM: Artificial sequence
<220> FEATURE:
<223> OTHER INFORMATION: Oligonucleotide OLPI FL

<400> SEQUENCE: 24
agctggcggc cgcttaatta agtggcgcgc caagctt    37

<210> SEQ ID NO 25
<211> LENGTH: 13
<212> TYPE: DNA
<213> ORGANISM: Artificial sequence
<220> FEATURE:
<223> OTHER INFORMATION: Sequence added in front of bovine 3 beta-HSDH

<400> SEQUENCE: 25

-continued gtcgacaaaa atg    13

<210> SEQ ID NO 26
<211> LENGTH: 24
<212> TYPE: DNA
<213> ORGANISM: Artificial sequence
<220> FEATURE:
<223> OTHER INFORMATION: End of the bovine 3 beta-HSDH cDNA

<400> SEQUENCE: 26
tgacctggag tgacaatgac gcgt    24

<210> SEQ ID NO 27
<211> LENGTH: 9
<212> TYPE: DNA
<213> ORGANISM: Artificial sequence
<220> FEATURE:
<223> OTHER INFORMATION: Oligonucleotide OTG5868

<400> SEQUENCE: 27 cgcgtgtac    9

<210> SEQ ID NO 28
<211> LENGTH: 28
<212> TYPE: DNA
<213> ORGANISM: Artificial sequence
<220> FEATURE:
<223> OTHER INFORMATION: Oligonucleotide OLIP 174

<400> SEQUENCE: 28
agctgcggcc gcggcgcgcc gtttaaac    28

<210> SEQ ID NO 29
<211> LENGTH: 28
<212> TYPE: DNA
<213> ORGANISM: Artificial sequence
<220> FEATURE:
<223> OTHER INFORMATION: Oligonucleotide OLIP 175

<400> SEQUENCE: 29
agctgtttaa acggcgcgcc gcggccgc    28

<210> SEQ ID NO 30
<211> LENGTH: 27
<212> TYPE: DNA
<213> ORGANISM: Artificial sequence
<220> FEATURE:
<223> OTHER INFORMATION: Oligonucleotide OLIP 21

<400> SEQUENCE: 30
aaacggcgca gtagggaata ttactgg    27

<210> SEQ ID NO 31
<211> LENGTH: 30
<212> TYPE: DNA
<213> ORGANISM: Artificial sequence
<220> FEATURE:
<223> OTHER INFORMATION: Oligonucleotide OLIP 22

<400> SEQUENCE: 31
ccgaagctta atcggcaaaa aaagaaaagc    30

<210> SEQ ID NO 32
<211> LENGTH: 12
<212> TYPE: DNA
<213> ORGANISM: Artificial sequence

```
<220> FEATURE:
<223> OTHER INFORMATION: Oligonucleotide OLIP 20

<400> SEQUENCE: 32
agctgcggcc gc                                                               12

<210> SEQ ID NO 33
<211> LENGTH: 22
<212> TYPE: DNA
<213> ORGANISM: Artificial sequence
<220> FEATURE:
<223> OTHER INFORMATION: Oligonucleotide C17-3

<400> SEQUENCE: 33
actgatggtt ggggtgcatt ga                                                    22

<210> SEQ ID NO 34
<211> LENGTH: 22
<212> TYPE: DNA
<213> ORGANISM: Artificial sequence
<220> FEATURE:
<223> OTHER INFORMATION: Oligonucleotide C17-5

<400> SEQUENCE: 34
atggcatcct ggaggttctg ag                                                    22

<210> SEQ ID NO 35
<211> LENGTH: 23
<212> TYPE: DNA
<213> ORGANISM: Artificial sequence
<220> FEATURE:
<223> OTHER INFORMATION: Oligonucleotide ADX-3

<400> SEQUENCE: 35
gtacccgggg atccttattc tat                                                   23

<210> SEQ ID NO 36
<211> LENGTH: 24
<212> TYPE: DNA
<213> ORGANISM: Artificial sequence
<220> FEATURE:
<223> OTHER INFORMATION: Oligonucleotide ADX-5

<400> SEQUENCE: 36
cagtccactt tataaaccgt gatg                                                  24

<210> SEQ ID NO 37
<211> LENGTH: 39
<212> TYPE: DNA
<213> ORGANISM: Artificial sequence
<220> FEATURE:
<223> OTHER INFORMATION: Oligonucleotide 5'ADE2090

<400> SEQUENCE: 37
cgattcggat ccactagtaa cgccgtatcg tgattaacg                                  39

<210> SEQ ID NO 38
<211> LENGTH: 40
<212> TYPE: DNA
<213> ORGANISM: Artificial sequence
<220> FEATURE:
<223> OTHER INFORMATION: Oligonucleotide 3'ADE2089

<400> SEQUENCE: 38
cctcaaggat cctcctgacg tagcgctatc ctcggttctg                                 40
```

```
<210> SEQ ID NO 39
<211> LENGTH: 327
<212> TYPE: DNA
<213> ORGANISM: Artificial sequence
<220> FEATURE:
<223> OTHER INFORMATION: Base of recombination R1

<400> SEQUENCE: 39
atggcccttc aagctgcttt ctttggtctc ctctgctttc tctgtccgca aagatggaaa      60
attaaatgct tcagcatcat catcattcaa agagtctagt ctgttcggtg tttcactttc     120
ggagcaaagc aaagctgact ttgtctcttc ctcattgaga tgcaagaggg aacagagctt     180
gaggaataat aaagcgatta ttcgagctca agcaatcgcg acttcaactc catcagtcac     240
aaaatcttcc ttagaccgca agaaaacact tagaaaagga acgtggttg tcacgggagc      300 ttcttcaggg ctaggtttag caacggc                                         327

<210> SEQ ID NO 40
<211> LENGTH: 336
<212> TYPE: DNA
<213> ORGANISM: Artificial sequence
<220> FEATURE:
<223> OTHER INFORMATION: Base of recombination R2

<400> SEQUENCE: 40
ataatggcgt gcagagactt cctcaaggct gagagagccg ctcaatctgc agggatgcct      60
aaggacagct acactatgat gcatttggac ttggcgtctt tggacagcgt gaggcagttt     120
gttgataact tcaggcgagc tgagatgcct ctcgatgtgt tggtctgcaa tgccgcagtc     180
tatcagccaa cggctaatca acctactttc actgctgaag gtttgagct agcgttggg       240 ataaaccatt tgggccactt tcttctttca agattgttga ttgatgactt gaagaactcc     300
gattatccat caaaacgtct catcattgtt ggtacc                               336

<210> SEQ ID NO 41
<211> LENGTH: 46
<212> TYPE: DNA
<213> ORGANISM: Artificial sequence
<220> FEATURE:
<223> OTHER INFORMATION: Oligonucleotide OTG10842

<400> SEQUENCE: 41
aaaaacgcgt aactattaaa gcgacgcaaa ttcgccgatg gtttgg                     46

<210> SEQ ID NO 42
<211> LENGTH: 50
<212> TYPE: DNA
<213> ORGANISM: Artificial sequence
<220> FEATURE:
<223> OTHER INFORMATION: Oligonucleotide OTG10841

<400> SEQUENCE: 42
aaaagtcgac aaaatggaag atatagaagg atacgaacca catatcactc                 50

<210> SEQ ID NO 43
<211> LENGTH: 20
<212> TYPE: DNA
<213> ORGANISM: Artificial sequence
<220> FEATURE:
<223> OTHER INFORMATION: Oligonucleotide arh1D

<400> SEQUENCE: 43
cggagcgcta tccttagaga                                                  20
```

<210> SEQ ID NO 44
<211> LENGTH: 20
<212> TYPE: DNA
<213> ORGANISM: Artificial sequence
<220> FEATURE:
<223> OTHER INFORMATION: Oligonucleotide nfs1R

<400> SEQUENCE: 44
acgtttcttt cgcctacgtg                                                 20

<210> SEQ ID NO 45
<211> LENGTH: 20
<212> TYPE: DNA
<213> ORGANISM: Artificial sequence
<220> FEATURE:
<223> OTHER INFORMATION: Oligonucleotide leu2D

<400> SEQUENCE: 45
ggtaaggcca ttgaagatgc                                                 20

<210> SEQ ID NO 46
<211> LENGTH: 20
<212> TYPE: DNA
<213> ORGANISM: Artificial sequence
<220> FEATURE:
<223> OTHER INFORMATION: Oligonucleotide arh1R

<400> SEQUENCE: 46 acccctttg ttccgagttc                                                  20

<210> SEQ ID NO 47
<211> LENGTH: 20
<212> TYPE: DNA
<213> ORGANISM: Artificial sequence
<220> FEATURE:
<223> OTHER INFORMATION: Oligonucleotide X1TEF1

<400> SEQUENCE: 47
ttcaaaacac ccaagcacag                                                 20

<210> SEQ ID NO 48
<211> LENGTH: 20
<212> TYPE: DNA
<213> ORGANISM: Artificial sequence
<220> FEATURE:
<223> OTHER INFORMATION: Oligonucleotide X2C21

<400> SEQUENCE: 48
ggtctgccag caaagtctgc                                                 20

<210> SEQ ID NO 49
<211> LENGTH: 20
<212> TYPE: DNA
<213> ORGANISM: Artificial sequence
<220> FEATURE:
<223> OTHER INFORMATION: Oligonucleotide X3TDH3

<400> SEQUENCE: 49
cgggcacaac ctcaatggag                                                 20

YEAST STRAINS AUTONOMOUSLY PRODUCING STEROIDS

The present invention relates to the production of steroids in microorganisms, in particular yeast strains.

Steroids, in particular cholesterol-derived steroids, are involved in many physiological processes, among which mention may be made of regulation of carbohydrates and cholesterol levels in the bloodstream, maintenance and development of muscle mass, and development of the central nervous system.

Among the drawbacks observed in the event of an imbalance of circulating steroid levels, mention may be made of the possible triggering of autoimmune diseases, such as lupus, of certain cancers, for example breast cancer, of cardiovascular diseases, for example atherosclerosis. Problems with steroid regulation are also suspected in the case of the triggering of certain neurological diseases, such as Parkinson's disease or Alzheimer's disease.

Steroids, in particular hydrocortisone, can be used as therapeutic agents as such or as supplements in other treatments. Thus, synthetic derivatives of glucocorticoids are used for their anti-inflammatory and, at high doses, immunosuppressive actions.

The production of steroids is partly associated with expensive methods of extraction or synthesis. John Warcup Cornforth was the first to carry out the complete synthesis of a steroid, cholesterol, using a enzymatic method. However, it is important to have a method for obtaining steroids of interest, in particular cholesterol derivatives, at an affordable price.

A certain number of proteins involved in steroid biosynthesis have been expressed in yeast. Thus, patent EP 360 361 demonstrates the activity of the proteins P450 17α and P450c21 in the yeast *Kluyveromyces lactis*. Similarly, the possibility of in vivo conversion of 11-deoxycortisol to hydrocortisone in a genetically modified yeast expressing P450c11 have been described (Dumas et al., 1996), as has the production of 17α-hydroxyprogesterone from pregnenolone in yeast (Degryse et al., 1999). In addition, Duport et al., (Duport et al., 1998) describe the synthesis of pregnenolone and progesterone in a genetically modified yeast. It has also been described, in patent application WO 99/40203, that inactivation of the ATF2 gene in a yeast strain makes it possible to avoid acetylation of the steroids produced by this strain.

The present invention makes it possible to carry out steroid synthesis, by fermentation of genetically modified yeast strains, in the presence of a simple carbon source. The method provided by the present invention therefore makes it possible to obtain a large amount of steroids of interest, at low cost, since the method uses fermentation of yeast and the addition of a simple carbon source which is readily commercially available.

DEFINITIONS

According to the present invention, the expression "simple carbon source" is intended to mean carbon sources which can be used by those skilled in the art for the normal growth of a yeast. It is in particular intended to denote the various assimilable sugars, such as glucose, galactose or sucrose, or molasses, or the byproducts of these sugars. A most particularly preferred simple carbon source is ethanol and glycerol.

According to the present invention, the term "steroid derivative" is intended to denote a compound which can be obtained, in particular with one or two enzymatic or chemical reactions, from said steroids. It is in particular intended to denote acetylated or hydroxylated steroids or steroids bearing a substituent such as a halogenated (fluorine, iodine) derivative, or a methyl group.

There are various types of problems to be solved in order to be able to produce steroids in a microorganism:

it is advisable to eliminate the parasitic reactions which may be observed due to the-presence of endogenous enzymes in the microorganism chosen, it is advisable to introduce the genes for modifying the synthesis intermediates such that the levels of expression obtained are as close as possible to the levels observed in mammals. Thus, recreating the correct balances is an important conditions for the success of such a project, it is advisable to obtain a level of expression of the various genes which makes it possible to preferentially direct the biosynthesis toward the chosen steroid.

Steroid synthesis is a series of extremely complex reactions involving several enzymes in order to obtain cortisol from cholesterol.

20,22-Dihydroxycholesterol should first be produced, which is then transformed into pregnenolone, itself hydroxylated to 17α-hydroxypregnenolone. This is then transformed into 17α-hydroxyprogesterone, which gives deoxycortisol, leading to cortisol (hydrocortisone).

An alternative pathway consists of the production of pregnenolone, and then of progesterone, transformed to 17α-hydroxyprogesterone.

It has been demonstrated that pregnenolone can be produced in yeast, from a simple carbon source (Duport et al., 1998, the content of which is incorporated into the present application by way of reference). To do this, it was necessary to delete an endogenous pathway (by disruption of the Δ22-sterol desaturase (ERG5) gene of the endogenous ergosterol biosynthesis pathway), in order to obtain an accumulation of C-22-saturated products. Specifically, the ergosterol normally produced by yeast differs from cholesterol by an unsaturation at C-7 (8) of the B ring, an unsaturation at C-22 and an additional methyl group at C-24. Thus, the products saturated at C-22 and at C-7 in the B ring can be used as substrates by the enzymes in the cortisol production chain.

The present invention makes it possible to synthesize steroids, and in particular the steroids located further downstream than pregnenolone, simply, by fermentation of genetically modified yeast strains, in the presence of a simple carbon source. In a particular case of the invention, the steroids synthesized are excreted into the culture medium, which simplifies the purification thereof. The method provided by the present invention therefore makes it possible to obtain a large amount of steroids of interest, at low cost, since the method uses fermentation of yeasts and the addition of a simple carbon source which is readily commercially available.

Preferably, the steroids which can be produced by the yeast strain according to the invention are steroids included in the cortisol synthetic pathway, as stated above. It is also possible to produce other types of steroids, from 17α-hydroxypregnenolone, in particular dihydroepiandrosterone (DHEA), by the action of the enzyme 17α-hydroxylase and lyase, and the derived steroids (androstenediones, testosterone, etc.). These steroids can be produced by introducing the appropriate enzymes into the yeast strain, in the same way as for the strain exemplified in the present invention.

In order to carry out the method according to the invention, the invention also relates to a genetically modified yeast strain producing a steroid or a steroid derivative, characterized in that it allows autonomous production from a simple carbon source.

The fact that the production is carried out autonomously means that there is no need to add substrates in order to obtain the steroid of interest, so that the yeast can produce it only from the starting simple carbon source. It is also clear that the strain can produce a steroid of the metabolic pathway, using a substrate located upstream in the metabolic pathway, insofar as the yeast strain according to the present invention contains all the genes required to complete the metabolic pathway for steroid production.

Preferably, the yeast strain according to the invention produces a steroid or steroid derivative which is a derivative of cholesterol metabolism, i.e. which is part of the cholesterol metabolic chain. Cholesterol metabolism is well known to those skilled in the art, and is explained in biochemistry and endocrinology publications.

Thus, preferably, said steroid or steroid derivative is in particular included in the group consisting of 17α-hydroxypregnenolone, cortisol, cortisone, cortexolone, 17α-hydroxyprogesterone, and derivatives of these steroids.

It is also possible to produce pregnenolone and progesterone with a yeast strain according to the present invention.

Thus, a subject of the present invention is in particular a genetically modified yeast strain autonomously producing, from a simple carbon source, a steroid or a steroid derivative, derived from cholesterol metabolism, characterized in that said steroid or steroid derivative is included in the group consisting of 17α-hydroxypregnenolone, hydrocortisone, cortexolone, 17α-hydroxyprogesterone, and derivatives of these steroids.

As will be seen later, the yeast strain according to the invention has at least one genetic modification chosen from a group consisting of disruption or inactivation of an endogenous gene, modification of the promoter of an endogenous gene, duplication of an endogenous gene, and introduction of at least one heterologous gene, in one or more copies, episomally or chromosomally.

It is, moreover, advantageous for the yeast strain of the invention to have a combination of said gene modifications.

As explained later, in a first embodiment, the yeast strain has at least one disruption of an endogenous gene chosen from the group consisting of ERG5, ATF2, GCY1, YPR1, ARE1, ARE2, ATF1 and ADE2.

In a preferred embodiment, the yeast strain according to the invention has a disruption of the endogenous genes ERG5, ATF2, GCY1 and YPR1. As described later, these genes encode proteins which induce parasitic reactions in the yeast.

With regard to the ADE2 gene, it may also optionally be disrupted, in particular in order to integrate a heterologous gene into the yeast strain.

In one embodiment, the yeast strain according to the invention has at least one heterologous gene integrated into the chromosome, at least one locus chosen from ADE2, HIS3, TRP1, LEU2, GCY1, ATF2 and YPR1, the integration being carried out intragenically or intergenically in the immediate vicinity of one of the loci.

In one embodiment of the invention, said yeast strain has at least one heterologous gene located on a multicopy plasmid or a low copy plasmid, said multicopy plasmid being chosen from yeast 2-micron replicon-based plasmids which replicate in Saccharomyces cerevisiae and said low copy plasmid being chosen from plasmids based on a chromosomal ARS origin of replication with a yeast centromere.

To implement an embodiment of the invention, and as developed below, the yeast strain according to the invention has at least one heterologous gene or cDNA chosen from the group consisting of the gene of sterol Δ7-reductase and of the cDNAs of cytochrome P450 SCC, of adrenodoxin, of adrenodoxin reductase, of cytochrome b5, of 3β-hydrosteroid dehydrogenase isomerase, of cytochrome P450 reductase, of cytochrome P450 C17, of cytochrome P450 C21 and of cytochrome P450 C11, and of the sequences encoding these proteins.

These heterologous genes or cDNAs are under the control of a promoter sequence chosen from the group consisting of the yeast endogenous promoter sequences TDH3, TEF1, PGK1, CYC1, GAL10, ATF2, TIR1, ARH1 and ADE2, and the hybrid promoter GAL10-CYC1.

It is necessary to use a terminator sequence for any heterologous gene or cDNA introduced, preferably chosen from the terminator sequences of the endogenous genes PGK1, CYC1, ATF2, ADE2 and NCP1.

Expression cassettes or blocks are then obtained, which consist of a promoter, the heterologous gene (or cDNA, optionally encoding the mature protein preceded by the ATG codon encoding methionine (Met-mat) or encoding a fusion protein optionally having signals for addressing to cellular compartments), and a terminator sequence.

In one embodiment, the yeast strain according to the invention has the sterol Δ7-reductase heterologous expression block integrated into the chromosome at the ADE2 locus.

In a particular embodiment of the invention, the yeast strain comprises at least one cassette for expression of the genes encoding $P450_{SCC}$ and adrenodoxin cofactor of $P450_{SCC}$, located on a high copy plasmid, and it comprises a cassette for expression of adrenodoxin reductase cofactor of $P450_{SCC}$, located on a single copy plasmid or a low copy plasmid or integrated into the chromosome. Preferably, these expression cassettes contain the mature protein preceded by a methionine, and the protein is located in the cytosol.

In one embodiment, the yeast strain comprises at least one expression cassette chosen from the cassettes for expression of 3β-hydrosteroid dehydrogenase isomerase, of cytochrome P450c17 or cytochrome P450c21, located on a high copy plasmid or a low copy plasmid or integrated into the chromosome.

In a particular embodiment, the yeast strain according to the invention comprises at least one expression cassette for P450 11β, located on a multicopy plasmid, the protein produced having a signal for addressing to mitochondria, and/or at least one expression cassette for adrenodoxin cofactor of P450 11β, located on a multicopy plasmid, with a weak promoter (i.e. the strength of which is related to that of the CYC1 promoter), the protein produced having a signal for addressing to mitochondria. Preferably, the proteins are produced in the form of a precursor, with a homologous or heterologous signal for addressing to mitochondria, the proteins taking their mature form in this cellular compartment.

It is therefore interesting to note that, in a particularly preferred embodiment of the invention, two copies of the gene encoding adrenodoxin are introduced into the yeast strain, one of them being intended to express the protein in the cytosol of the cell, the other being produced such that the mature protein is in the mitochondria.

In a particular embodiment, the yeast strain also comprises at least one expression cassette (expression promoter as mentioned above with the coding portion of the NCP1, ATR1 and/or ATR2 gene, with its own terminator or terminator as defined above) located on a multicopy plasmid or low copy plasmid or integrated into the chromosome. The expression cassettes for NCP1, ATR1 and ATR2 may in particular be integrated at the NCP1 locus of S. cerevisiae.

In a particular embodiment, the yeast strain according to the invention also expresses the ARH1p protein, a protein homologous to mammalian adrenodoxin reductase in yeast, at a level higher than the physiological expression level. Overexpression of this protein can be obtained using techniques well known to those skilled in the art, for example by introducing a new expression cassette (expression promoter, coding portion of the ARH1 gene with its own terminator or a terminator as defined above), in addition to the endogenous gene, into the yeast. Surprisingly, it has indeed been shown that expression of the ARH1 gene at a level higher than the physiological expression level significantly increases the amount of steroids produced. However, this expression should not be too great to obtain the desired effect. Thus, if an expression of the ARH1 protein at a level higher than a physiological level is desirable, care should be taken not to overexpress this protein too strongly, otherwise there is a risk of losing this increase in production of steroids.

The yeast strain according to the present invention may be polyploid, diploid, haploid or aneuploid in nature, without this being harmful to the implementation of the invention.

It is preferably a strain of *Saccharomyces cerevisiae*, in particular derived from one of the strains FY 1679-28c and FY 1679-18b which are spores of the strain FY 1679 deposited with the American Type Culture Collection under the number 96604.

A subject of the invention is also a yeast strain, characterized in that it is the strain CDR07 Mat-α or TGY260, deposited with the CNCM on Jan. 24, 2001, under the respective accession numbers I-2616 and I-2615. The invention also relates to a strain obtained after crossing of CDR07 Mat-α and TGY260, and optionally sporulation and transformation with a plasmid from yeast, in particular the strains UCY2 and UCY4 and the strains UCY3 and UCY26 described in the present invention. A subject of the invention is also yeast strains obtained after crossing of UCY2 and TGY245, and optionally sporulation and transformation with at least one plasmid from yeast, in particular the strains UCY5, UCY6, UCY16, UCY19, UCY20, UCY24, UCY25 and UCY26, also described in the present invention.

It is useful for the yeast strain according to the invention to have the elements required for excreting the steroid produced into the culture medium, in order to simplify purification of the final product.

The invention also relates to a method for producing a steroid, characterized in that it comprises the steps of fermenting a yeast strain according to the invention in the presence of a simple carbon source, and of recovering the steroid produced.

Finally, the subject of the invention is also a pharmaceutical preparation comprising a yeast strain according to the invention, optionally with a pharmaceutically acceptable excipient, such an excipient being well known to those skilled in the art.

Although the yeast strain according to the invention produces a steroid autonomously from a simple carbon source, it is also possible to provide it with cholesterol or a related structure, or a substrate already present as a cholesterol derivative, in order to obtain the products located downstream. The possibility of being able to enter at any stage, in particular at the pregnenolone level or later in the metabolic pathway of the desired steroid therefore makes it possible in particular to be able to provide the yeast with unnatural substrates, which lead to the synthesis of unnatural and substituted steroids, in particular fluorinated steroids.

In a first embodiment, the yeast strain according to the present invention in particular makes it possible to produce the desired steroid (in particular cortisol) in an amount greater than 10 mg/l, preferably greater than 50 mg/l, more preferably 80 mg/l, more preferably 100 mg/l, and most preferably 200 mg/l.

In another embodiment, the steroid of interest (preferably hydrocortisone) is present in a proportion greater than 20%, preferably 25%, more preferably 30%, more preferably 35%, more preferably 40%, more preferably 50%, and most preferably 65%, of the total steroids produced by the strain according to the invention (in particular the synthesis intermediates).

In order for it to be possible for the yeast strain according to the present invention to produce the steroids of interest, it is necessary for it to have genetic modifications. Thus, the yeast strain according to the invention has at least one genetic modification chosen from the group consisting of disruption or inactivation of an endogenous gene, modification of the promoter of an endogenous gene, duplication of an endogenous gene, and introduction of at least one heterologous gene (in particular an expression block with homologous promoter and/or terminator and a heterologous coding portion), in one or more copies, episomally or chromosomally.

Preferably, the yeast strain according to the invention has several (at least four) genetic modifications as stated above.

Thus, some endogenous genes of the yeast are favorably inactivated or disrupted. The genes can be inactivated or disrupted by introducing, into the coding sequence, an exogenous gene (in particular an expression block with homologous promoter and/or terminator and a heterologous coding portion) as described below, and/or a selectable marker. It is also possible to modify the promoters of these genes in order to decrease the level of expression.

The yeast gene ATF2 (Cauet et al., 1999) encodes an acetyl transferase which uses pregnenolone as substrate, and disruption thereof makes it possible to eliminate this parasitic acetylation reaction, the product of which cannot then be used, and thus to increase the yield of steroid of interest. Thus, the yields can be multiplied by values of between 3 and 7 after inactivation of the ATF2 gene.

The GCY1 and YPR1 genes encode aldo-keto reductases. These genes—are advantageously inactivated or disrupted. These two genes are part of a family of 6 more or less homologous genes, all six of which are supposed to encode aldo-keto reductases. However, the products of these genes are the most active on the substrates envisioned herein, in particular GCY1, and inactivation thereof is therefore extremely advantageous for obtaining hydrocortisone.

As specified above, it is advantageous to inactivate the ERG5 gene in order to accumulate a substrate which has a structure as close as possible to the structure of cholesterol. However, it has been shown that the yeast according to the invention can, nevertheless, produce the steroids of interest despite the activity of this gene. However, in order to optimize yields, it may be useful to inactivate it by mutation, deletion and/or insertion.

It is also possible, without this being really essential for the overall success of the steroid production with the yeast according to the present invention, to inactivate other genes, such as ARE1, ARE2, ADE2 or ATF1. These genes all encode proteins the absence of which may improve the overall yield of synthesis of the steroid of interest.

As described in the article by Duport et al., cited above (Duport et al., 1998), it is indicated that the presence of an expression block with homologous promoter and/or terminator and a sequence encoding Δ7-reductase is useful in that it makes it possible to desaturate the 7-8 double bond of ergosterol and of its derivatives, and thus to obtain one or more precursors with a structure closer to the structure of cholesterol, the starting substrate for the production of pregnenolone. Thus, it is advantageous for the yeast strain according to the present invention to contain this expression block. In a particular case, said block for expression of Δ7-reductase is integrated into the genome of the yeast, preferably at the locus of the ADE2 gene, by the same token leading to the disruption of the ADE2 gene. The promoter used for transcription is an inducible promoter, such as GAL10-CYC1, or a constitutive promoter, such as the GAL10-GAL10-CYC1 promoter which is disrupted in the strain CA10 described in Duport et al., 1998. The protein used is preferentially derived from *Arabidopsis thaliana* (but may also be derived from a mammalian species), the cDNA being cloned in the native form (complementary DNA just after a translation initiation methionine), and under the control of a transcription terminator which is conventional in yeast, such as PGK1.

It should be noted that activity of the Δ7-reductase gene in yeast has been described by Lecain et al., 1996, the technical content of which (in particular the sequences of the Δ7-reductase gene and the constructs and procedures) is incorporated into the present application by way of reference.

The first step is the production of pregnenolone, obtained after introducing into the yeast the enzymes for normally transforming cholesterol into pregnenolone. In the present case, this is the enzyme for cleaving the side chain ($P450_{SCC}$ for side chain cleavage), with two co-enzymes (adrenodoxin, ADX, and adrenodoxin reductase, ADR). The transformation of the yeast with these respective expression blocks is described in Duport et al., 1998, cited above.

A complementary DNA encoding the mature proteins, with a methionine added to the N-terminal end to allow translation, is preferably used. Promoters such as the GAL10-CYC1 hybrid promoter or the TEF1 promoter are used to ensure transcription of the cDNAs. Conventional terminators, in particular the PGK1 terminator, are used.

The various cDNAs encoding the $P450_{SCC}$, ADR or ADX proteins may be of vertebrate origin, for example human or bovine origin, but also rat or fish. The genes encoding these proteins are preferably placed on plasmids; for $P450_{SCC}$ and ADX, a multicopy low copy or high copy plasmid, in particular derived from a 2 micron yeast plasmid, is preferred, whereas a single copy plasmid or a low copy plasmid is rather used for the expression of ADR. The expression block for ADR may also be integrated into the chromosome of the yeast. This makes it possible to control expression of the ADR, since is appears that too much expression harms the desired scc activity.

The proteins are preferably expressed so as to be able to exert their activity in the cytosol.

The following step is the conversion of pregnenolone to 17α-hydroxyprogesterone, by the combined action of 17α-hydroxylase (P450c17) and 3β-hydroxysteroid dehydrogenase (3β-HSD).

To express these two proteins, strong promoters, such as TEF1, TDH3 or GAL10-CYC1, are preferably used. However, a weaker promoter, such as CYC1, may also be suitable. The terminators used are conventional, and in particular come from the PGK1 or NCP1 genes. The complementary DNAs encoding the complete proteins are expressed. The species of origin of these proteins does not appear to modify the results obtained, and it is thus possible to use proteins of human origin (in particular one or other of the two isotypes of 3β-HSD), of bovine origin or originating from other organisms (in particular from fish). For these two proteins, it is a question of obtaining the best possible expression, and they can therefore be expressed on single copy or multicopy, low copy or high copy plasmids, or by having integrated the expression blocks into at least one chromosome of the yeast.

Conversion of the 17α-hydroxyprogesterone to deoxycortisol is then sought, via P450c21, which allows hydroxylation at position 21. It is a question of expressing the protein from its cDNA in the most effective way possible. To do this, a strong promoter (TEF1, TDH3, GAL10-CYC1, etc.), or even the CYC1 promoter, and a conventional terminator (in particular PGK1) are used to design the transcriptional unit. This unit is placed on a single copy or multicopy, low copy or high copy plasmid, or else integrated into the genome of the yeast. It should be noted that the species of origin appears to be important here, and that it is preferable to use P450c21 of human origin.

The deoxycortisol is then converted to cortisol, under the action of the P450c11 system, which contains P450c11, allowing hydroxylation at the 11-β position, and an adrenodoxin and an adrenodoxin reductase as cofactors.

The inventors of the present application have shown that the results obtained are better when this last system is expressed in the inner membrane of yeast mitochondria. Thus, it is advantageous to produce fusion proteins which carry, as precursor, the mitochondrial addressing sequence of the yeast Cox6p protein precursor.

The cDNA encoding the mature proteins is also preferably used. The P450c11 protein is thus the protein of human or bovine origin or a human-bovine hybrid protein. The latter construct is the preferred form for implementing the invention. The gene used in the transcriptional unit is preferably under the control of the CYC1 promoter. It is advantageous to place a rabbit β-globin intron and a terminator of the human growth hormone gene in the position 3' of the coding sequence. The transcriptional unit is preferably placed on a multicopy plasmid.

The adrenodoxin is used in its mature form, placed with a sequence for addressing to mitochondria, for example chosen from those of the percursors of the Cox6p, Cox4p, fumarase, ARH1p and F9 ATPase proteins, and under the control of a promoter in particular chosen from TDH3, TEF1 and CYC1. A protein of bovine or human origin is preferred. A terminator, which may be PGK1, should be placed in the transcriptional unit. The expression block is preferably expressed from a multicopy plasmid.

The proteins acting as an adrenodoxin reductase is the ARH1p protein, an endogenous yeast protein, which is normally expressed in the host's mitochondria. Preferably, the yeast is, however, transformed in such a way that the host strain contains a natural copy of the ARH1 gene and a second copy of the ARH1 gene under the control of the CYC1 promoter. The activity of this protein is essential for obtaining the desired effect, and it has even been observed that inactivation of the gene is lethal for yeast (Lacour et al., 1998). It should be noted that overexpression of this gene appears to be toxic for the organism, and that the promoter chosen should therefore allow a level of expression which leads to the desired 11-β hydroxylase activity without being deleterious for yeast. Surprisingly, it has in fact been shown that expression of the ARH1 gene at a level higher than the physiological expression level significantly increases the amount of steroids produced. However, as mentioned above, this expression should not be too great to obtain the desired effect. Thus, if expression of the ARH1 protein at a level greater than a physiological level is desirable, care should be taken not to overexpress this protein too strongly, otherwise there is a risk of losing this increase in production of steroids. By way of example, integration of the expression cassette for ARH1, comprising as promoter the CYC1 promoter, at the LEU2 locus of *S. cer-* evisiae gives satisfactory levels of expression and results. On the other hand, integration, at the same locus, of a cassette comprising the TEF1 promoter, acknowledged to be much stronger than the CYC1 promoter, gives less advantageous results.

Thus, two copies of a transcriptional unit encoding the ADX co-enzyme protein are preferably introduced, one of them having activity outside the mitochondria, and in particular in the cytosol, the other having activity in the mitochondria of the host cell.

It is also possible to introduce other genes, in particular the genes encoding proteins having NADPH P450 reductase activity, such as NCP1 (yeast reductase also called CPR1), ATR1 or ATR2 (plant reductases), or human reductase. These proteins improve P450c17 and P450c21 activities. Either the endogenous promoter (NCP1) is used, or the DNAs encoding the proteins are placed under the control of promoters such as GAL10-CYC1, CYC1, TEF1, etc.

It is also possible to introduce the TGL1 gene, which encodes a protein having deesterification activity, under the control of a strong promoter such as GAL10-CYC1, on a multicopy or single copy plasmid. This makes it possible to reduce the effect of parasitic reactions of sterol esterification which may remain even after inactivation of ATF2, and in particular those produced by the product of the ARE1 and ARE2 genes.

It is also possible to add a plasmid expressing cytochrome b5 from yeast or another species, which is a cofactor in several of the reactions defined above.

When it is desired to produce DHEA, it is also possible to introduce a low or high copy plasmid encoding desmolase (P450 17α), under the control of a promoter such as GAL10-CYC1, CYC1 or TEF1, with a PGK1 terminator.

It is also possible to introduce a cDNA encoding cytochrome P450c17 having lyase activity, for example that of human origin, in the presence of an excess of NADPH P-450 reductase, for instance mammalian reductases, NCP1, ATR1 or ATR2. These transcriptional units preferably use a strong promoter.

Finally, it is possible to restore the activity of the endogenous ERG6 and ERG2 genes, inhibited by pregnenolone, by placing them under the control of a strong constitutive promoter.

It is also possible to introduce other heterologous genes, in particular encoding a protein with 24,25 sterol reductase activity, or the HMG1 gene, present in the synthetic path with cholesterol in humans. It is also advantageous to introduce the human MDR1 gene, which encodes a pump which is not inhibited by accumulation of the abnormal sterols which appear due to the inhibition of the ERG6 gene by pregnenolone. This makes it possible to expel these products, too great an accumulation of which might prove to be toxic for the host cell.

It is also possible to overexpress the yeast PDR12 gene, which will have a detoxification effect for the steroids which may inhibit the yeast growth.

It is understood that, when reference is made to "gene" above, this is intended to mean not only the DNA fragment encoding the protein having the desired activity (and especially the cDNA fragment representing in particular the mature forms), but also the promoters (in particular TEF1, GAL10-CYC1, CYC1, TDH3) and the terminators (in particular the PGK1). These transcriptional units are preferentially introduced on low or high copy plasmids, or integrated into the chromosome of the yeast.

It is also understood that, depending on the desired aim, and in particular the steroid that is intended to be produced, it is possible to introduce only some of the genes encoding the various proteins of each step, and to provide the yeast with an intermediate in order to obtain a steroid which is downstream in the metabolic chain.

It is also easy not to introduce the genes for obtaining the products located downstream, and therefore to be able to stop relatively high in the metabolic chain.

The yeast used to implement the present invention is preferably:—the FY1679-28c strain, described in Duport et al., 1998, which has the genotype (MATα, rho⁻, ura3-52, trp1Δ63, leu2 Δ1, his3Δ200, GAL2, fen1). This strain has also been described by Thierry et al., 1990;

the FY1679-18b strain, having the genotype (MATa, rho⁻, ura3-52, trp1Δ63, leu2 Δ1, his3Δ200, GAL2, fen1).

These two strains therefore have an identical genotype and an opposite sign.

EXAMPLES

Figure 1:
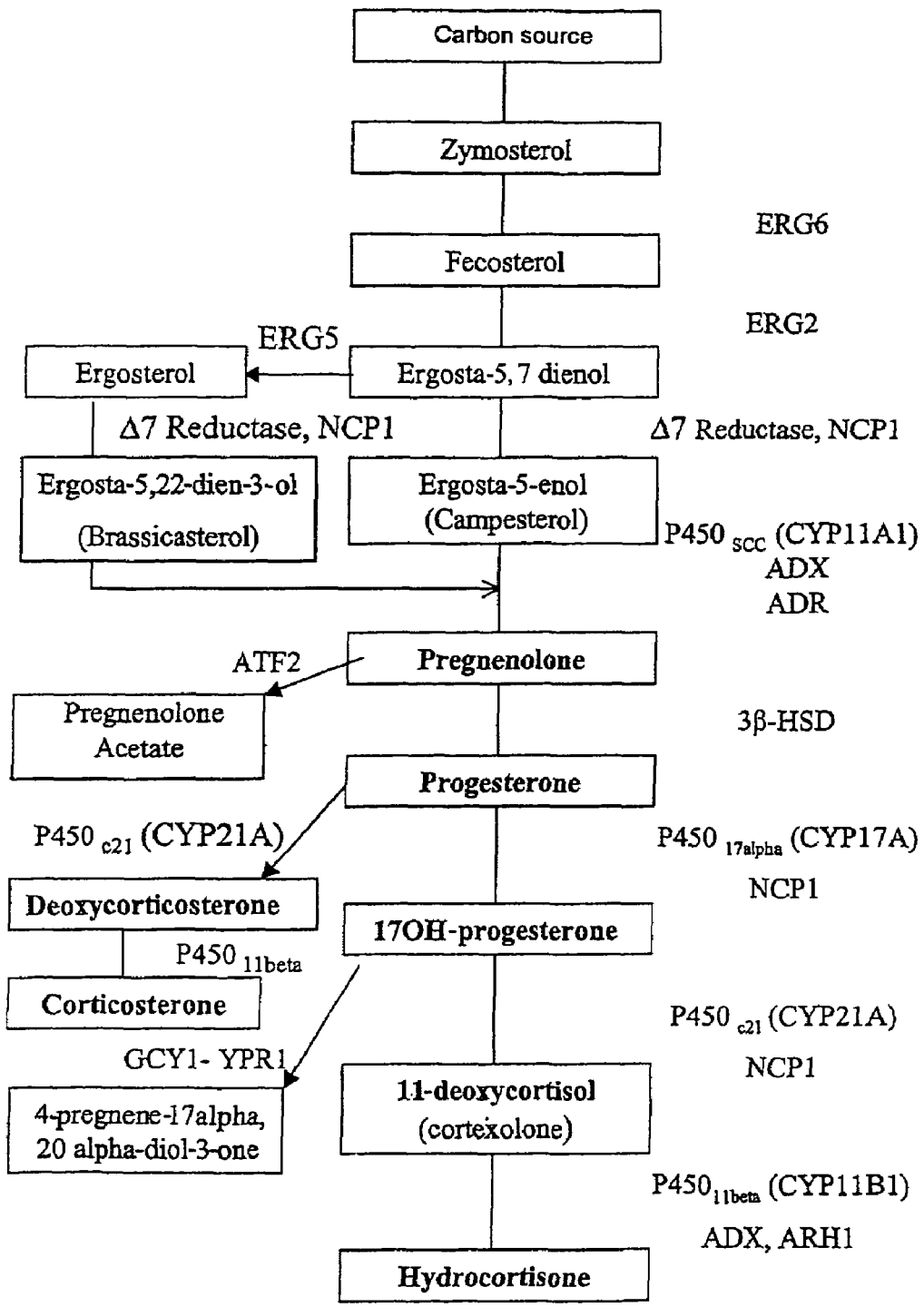
FIG. 1: Diagrammatic representation of a biosynthetic pathway for hydrocortisone as can be obtained according to the invention.

The examples below describe an embodiment of the present invention and should not be considered as limiting the invention.

For the constructions, the FY1679-28c and FY1679-18b yeast strains described above are used as starting materials.

Example 1

Disruption of the YPR1 Gene

The construct comprising interruption of the YPR1 gene (YDR368w) by the URA3 gene in the plasmid pPOLYIII was obtained by 4 successive PCR5. First, three independent PCR5 were carried out to obtain the 5' portion of the YPR1 gene (PCR 5), the functional URA3 gene bordered by YPR1 sequences (PCR 6), and the 3' portion of the YPR1 gene (PCR 7).

The PCR5 DNA was obtained by amplification on a genomic DNA matrix with the oligonucleotides OTG11314 (SEQ ID No. 1) and OTG11315 (SEQ ID No. 2) and, similarly, the PCR7 DNA is obtained by amplification using the oligonucleotides OTG11316 (SEQ ID No. 3) and OTG11317 (SEQ ID No. 4) on the same matrix.

The URA3 gene flanked by 5' and 3'YPR1 region is amplified using the oligonucleotides OTG11463 (SEQ ID No. 5) and OTG11464 (SEQ ID No. 6) on a matrix pTG10054 described in Degryse et al., 1995, incorporated herein by way of reference as regards the description of this plasmid.

The products of PCR5, PCR6 and PCR7 were mixed in an equimolecular—fashion and then amplified by PCR using the oligonucleotides OTG11314 (SEQ ID No. 1) and OTG11317 (SEQ ID No. 4), so as to obtain a product of PCR8.

This PCR8 product was digested with the XhoI enzyme and then subcloned into the plasmid pPOLYIII (described by Lathe et al., 1987, and incorporated herein by way of reference as regards the description of this plasmid) digested with XhoI, to give the plasmid pTG12011. The orientation of the insertion into the plasmid pPOLYIII was determined by digestion with the NcoI and EcoRI enzymes.

The plasmid pTG12011, which allows disruption of the parasitic YPR1 gene with the URA3 gene, is digested with the XhoI enzyme. The digestion product is used to transform the FY1679-18b strain using the lithium chloride method well known to those skilled in the art. The transformants are selected on a uracil-free medium. The transformants are analyzed by PCR amplification using the oligonucleotides which were used to construct the plasmid pTG12011.

The clones which are positive in this test are then screened by the 17OH-progesterone bioconversion method described below, in the presence of glucose as carbon source. The capacity for bioconversion is analyzed by HPLC as described by Dumas et al., 1996 and Degryse et al., 1999, the contents of which are incorporated into the present application by way of reference, in particular the explanations of the bioconversion studies, or as described in Kuronen at al., 1999. A clone, TGY195#4, is selected for further characterizations. The TGY195#4 strain is transformed using both the plasmid YRp7 (Parent et al., 1985, which is incorporated by way of reference as regards the description of this plasmid) (1 µg) and 5 µg of plasmid pTG12045 (described below) digested with NotI. The transformed strains are selected on a tryptophan-free medium. Colonies (678 colonies) are subcultured on a medium containing trytophan (so as to eliminate the plasmid YRp7) and on a medium containing tryptophan and 5-fluoroorotate (5F0) in order to select the colonies which have lost the URA3 gene interrupting the YPR1 gene.

Example 2

Construction of Various Plasmids

For overexpression of the P450c21 protein in yeast two types of promoter were used, TEF1 (transcription elongation factor 1) and TDH3 (glyceraldehyde-3-phosphate dehydrogenase 3). In all cases, the transcription terminator is the PGK terminator. In these plasmids, the SalI, MluI fragment carries the human P450c21 cDNA.

a) Construction of the Plasmids pTG10470 and pTG10469

The plasmid pTG10289 was obtained by modification of pMAc21 (Wu et al., 1991) by digestion with KpnI and MluI and introduction of the oligonucleotide OTG5868 (SEQ ID No. 27).

The cDNA of this plasmid comes from the American Type Culture Collection (ATCC, Manassas, Va., USA) under the name pc21/3c. It is the 1.6 Kb EcoRI-BamHI fragment which was used as a base to construct the various plasmids. The modifications introduced are described in the article above and in the article by Hu et al., 1990.

In this procedure, the noncoding portion of P450c21 of the plasmid pMAc21 which contains the expression cassette for p450c21 was removed, as was the KpnI site located therein.

The plasmid pTG10292 was obtained by transferring the human c21 cDNA (SalI, MluI fragment) of the plasmid pTG10289 into the plasmid pTG10031 (described in Degryse et al., 1995, which is incorporated into the application by way of reference) using the SalI and MluI sites.

The plasmid pTG10475 was obtained by PCR and recombination. Specifically, using the plasmid pTG10292, a fragment of the human P450c21 cDNA representing approximately 250 nucleotides was amplified using the oligonucleotides OTG7410 (SEQ ID No. 7) and OTG5927 (SEQ ID No. 8). This fragment represents the coding sequence of human P450c21, of a SalI site and of the sequence AAAA.

This fragment was digested with SalI and then ligated onto the linear fragment of pTG10292 digested with SalI, and the recombination experiment was then carried out in the BJ5183 strain described by Degryse et al., 1995.

The plasmid obtained, pTG10475, carries a P450c21 cDNA with a coding sequence identical to that of the natural cDNA, unlike the plasmid pMAc21, on a fragment compatible with the vectors generally used by the inventors, i.e. a fragment bordered by the SalI and MulI restriction sites. This fragment has the following environment around the ATG codon for translation initiation: GTCGACAAAAATGCT-GCTCCTGGGCCTGCTGC (SEQ ID No. 9).

Using this plasmid, the SalI, MulI fragment carrying the human p450c21 cDNA was transferred into the plasmid pTG10158 (Degryse et al., 1995) by conventional cloning, to give the plasmid pTG10472.

This same SalI, MluI fragment of the plasmid pTG10472 was then transferred by conventional cloning into the plasmid pTG10085 (Degryse et al., 1995), to give the plasmid pTG10469. This plasmid therefore has the human P450c21 cDNA under the control of the TEF1 promoter, with the PGK1 terminator.

This same fragment carrying the P450c21 cDNA on a SalI and MluI restriction fragment is transferred into the plasmid pTG10092 by recombination in the BJ5183 strain, to give the plasmid pTG10470 (Degryse et al., 1996).

The plasmid pTG10470 therefore carries the human P450c21 cDNA under the control of the TEF1 promoter and of a PGK1 terminator, with a URA3-d selection marker with the environment of the ATG initiator codon described above.

b) Construction of the Plasmid pTG12036

The plasmid pTG12036 was constructed in 4 steps from pTG10802. The plasmid pTG10801 (which is the origin of the plasmid pTG10802) is a plasmid of the pUC type into which a series of restriction sites has been inserted between the XhoI and XhoI sites. This series of sites includes the HindIII, SnabI, ClaI and SpeI sites.

Between the HindIII and ClaI sites, the HindIII, ClaI cassette of pTG10470, comprising the TEF1 promoter, the human P450c21 cDNA and the PGK1 terminator, was inserted between the HindIII and ClaI sites of pTG10801, to give pTG10802.

This plasmid was then digested with XhoI and the cassette introduced is therefore deleted in order to introduce a PCR fragment bordered by XhoI sites. This 2.5 Kb fragment comes from amplification with the pair of oligonucleotides OTG11844 (SEQ ID No. 10) and OTG11845 (SEQ ID No. 11) on the plasmid pTG12010#40 (cf. below) so as to obtain a fragment bordered by XhoI sites, containing the GCY1 gene interrupted by the URA3 gene bordered in the 5' position by a ClaI restriction site.

This fragment was cloned between the XhoI sites of the plasmid pTG10802, so as to obtain the plasmid pTG12035. The plamid pTG12010#36 was used with the aim of introducing the missing HindIII site. This plasmid is essentially identical to pTG12010#40, but has a HindIII site positioned 3' of the URA3 gene at the limit with the GCY1 gene, but does not have a ClaI site positioned 5' of the URA3 gene at the junction with the GCY1 gene (cf. below). By recombination in vivo in E. coli, between the 2.2 Kb NcoI, BamH1 fragment which carries from 5' to 3' a fragment of the URA3 gene, the 3' fragment of the GCY1 gene and, finally, a portion of the plasmid pTG12035, i.e. the large 4.45 Kb StuI, AflII fragment. The plasmid pTG12036 is obtained.

The plasmid obtained, pTG12036, has the GCY1 gene interrupted by the URA3 gene bordered by ClaI and HindIII sites in 5' and 3' position, respectively. This fragment is then replaced with the expression cassette for P450c21 carried by the 2.33 Kb ClaI, HindIII fragment of the plasmid pTG10469 (see above), so as to obtain the plasmid pTG12086.

c) Construction of the Plasmid pTG12045

The unique SphI site of the plasmid pPOLYIII is destroyed by insertion of the pair of complementary oligonucleotides OTG11975 (SEQ ID No. 12) and OTG11976 (SEQ ID No. 13).

The SphI site of pPOLYIII is destroyed and replaced with a ClaI site, to give the plasmid pTG12040. A ClaI, EcoRI genomic DNA fragment corresponding to the 0.7 Kb 3' portion of the YPR1 gene obtained by amplification with the oligonucleotides OTG11981 (SEQ ID No. 14) and OTG11982 (SEQ ID No. 15) is introduced into the plasmid pTG12040, between the unique ClaI and EcoRI sites, to give the plasmid pTG12041.

In this 2.84 Kb plasmid pTG12041, the 5' portion of the YPR1 gene (0.66 Kb), amplified by the oligonucleotides OTG11314 (SEQ ID No. 1) and OTG11980 (SEQ ID No. 16) from wild-type yeast genomic DNA, is cloned in the form of an XhoI, HindIII fragment, between the SalI and HindIII sites of the plasmid pTG12041.

The 3.5 Kb plasmid pTG12042 is obtained. This plasmid carries the YPR1 gene interrupted by the ClaI and HindIII sites. The cytochrome P450c21 cassette is cloned between these sites, in the form of a 2.33 Kb ClaI, HindIII fragment originating from the plasmid pTG10469. The plasmid pTG12045 is thus obtained.

d) Construction of the Plasmids pTG12010#36 and #40

The plasmid pTG 12010 was constructed based on the plasmid pUC19 (Yanisch-Perron et al., 1985), whereas the plasmid pTG12011 was constructed based on the plasmid pPOLYIII (Lathe et al., 1987).

The construct comprising the disruption of the GCY1 gene by the URA3 gene in the plasmid pUC19 was obtained by four successive PCR amplifications. First, three independent PCR5 were carried out so as to obtain the 5' portion of the GCY1 gene (PCR1), the functional URA3 gene bordered by GCY1 sequences (PCR2), and the 3' portion of the GCY1 gene (PCR3).

The 5' and 3' portions of the GCY1 gene [lacuna] using the pairs OTG11285, OTG11286 and OTG11287, OTG11289 (respectively SEQ ID No. 17 to SEQ ID No. 20) on a matrix of genomic DNA of the FY1679-28c strain.

The URA3 gene flanked by GCY1 sequences (in such a way as to obtain a deletion of part of the coding sequence of the GCY1 gene) is amplified using the oligonucleotides OTG11305 (SEQ ID No. 21) and OTG11306 (SEQ ID No. 22) from a linearized plasmid pTG10054 matrix (Degryse et al., 1995).

The buffer conditions and matrix and primer concentration conditions for the amplification are described by the producer or manufacturer of the Taq DNA polymerase enzyme, and in particular for the elongase enzyme developed by Life Technologies. The temperature cycles are as follows: a first cycle of 6'30 to denature primer and matrix, and then 30 cycles of 30 s at 93° C., 2 min at 54° C. and 3 min at 68° C., and the final cycle is 5 min at 72° C. The PCR1, PCR2 and PCR3 products are mixed in an equimolecular fashion and amplified again using the oligonucleotides OTG 11285 (SEQ ID No. 17) and OTG11289 (SEQ ID No. 20). The final product, PCR4, which is 2.9 Kb in size, is then subcloned between the KpnI and BamHI restriction sites of the plasmid pUC19, so as to obtain the plasmid pTG12010.

The structure of the plasmid was verified by restriction profile and nucleotide sequencing of the ends.

Cloning pTG12010 in fact made it possible to obtain two versions of this plasmid, version pTG12010#40 (pTG12040 clone 40) and pTG12010#36. The initial desire was to obtain the GCY1 gene interrupted by the URA3 gene bordered by the ClaI and HindIII sites respectively positioned 5' and 3' of the gene. In fact, two different plasmids were obtained, which differ only by the presence or absence of ClaI and HindIII sites at the ends of the URA3 gene. The plasmid pTG12010#40 has a HindIII restriction site at the 3' end of the URA3 gene, but no ClaI site positioned 5'. The plasmid pTG12010#36 has no HindIII site at the 3' end, but a ClaI site at the 5' end of the gene. This property is used to obtain the plasmid which has the URA3 gene bordered by the HindIII and ClaI sites, interrupting the coding sequence of GCY1.

e) Construction of the Plasmid pTG12086

This plasmid is used to integrate an expression cassette for P450c21 and also to disrupt the GCY1 gene at the same time. This plasmid was constructed from the plasmid pTG12036 and from the plasmid pTG10614.

The construction of the plasmid pTG10614 was carried out as follows. This plasmid was constructed from the pTG10212 (Degryse et al., 1995), which is a yeast expression plasmid based on a TDH3 promoter, a PGK1 terminator and a URA3-d selection marker.

The selection marker is replaced with the selection marker of the plasmid pTG10054 (Degryse et al., 1995) by homologous recombination in E. coli; to do this, the 2.1 Kb MluI, FspI fragment of pTG10054 containing the URA3 marker flanked by recombination sequences is recombined with the large HindIII fragment of pTG10212, to give the plasmid pTG10610 which has the same characteristics as pTG10212 (Degryse et al., 1995) with a URA3 marker in the same orientation as pTG10054.

The SalI, MulI fragment carrying the human cytochrome P450c21 cDNA of the plasmid pTG10472 (cf. above) is transferred into the plasmid pTG0610, to give the plasmid pTG10614.

The ClaI, HindIII fragment of this plasmid containing, from 5' to 3', the TDH3 promoter, the human P450c21 cDNA bordered by SalI and MluI sites, and then the PGK1 terminator is transferred into the plasmid pTG12036, to give the plasmid pTG12086 which therefore contains the sequence of the GCY1 gene interrupted by the TDH3 expression cassette for human cytochrome P450c21.

f) Construction of the Plasmid pTG12048

The plasmid pTG12048 was constructed from the plasmids pFL26CD, pTG10925 and pTG10953.

pTG10953 is identical to the plasmid described in Lacour et al., 1998, but the TEF1 promoter which is carried by a ClaI, SalI fragment is replaced with a CYC1 promoter (Degryse et al., 1995). The expression cassette is carried by a NotI-NotI DNA fragment.

The plasmid pTG10925 was constructed from pFL26CD described by Duport et al., 1998. The plasmid contains a genomic fragment of yeast which comprises the LEU2 and NFS1 genes in 5' to 3' and 3' and 5' orientation respectively. An expression cassette for ADR bordered by NotI sites was introduced into the intergenic region to give the plasmid pTG10925. This cassette (TEF1-mature bovine ADR-PGK1 terminator) was replaced with a new cassette comprising the ARH1 gene under the control of the CYC1 promoter and the PGK1 terminator, to give the plasmid pTG12048. On this plasmid the LEU2 gene and the expression cassette are in the same transcriptional orientation.

Example 3

Construction of the TGY212#1 Strain

A colony is selected in the screen described in example 1. It is named TGY212#1. This colony is subjected to a bioconversion experiment as described previously with 100 µg/ml of 17OH-progesterone substrate, and the strain is allowed to grow in a minimum medium supplemented with required amino acids and uracil.

This strain is capable of converting 17OH-progesterone to 11-deoxycortisol with an efficiency of the order of 47% over the course of 24 hours with weak production of 4-pregnene-17α,20α-diol-3-one under these conditions (<0.5%). Under certain conditions (defined rich medium of the Kappeli type with galactose as carbon source and culture started at high density: OD 600 nm=5), the capacity for reduction of the ketone is increased to reach 11% of the starting substrate with a capacity for bioconversion reduced to 1.5% of the starting substrate.

Under these conditions, the probable presence of the GCY1 gene constitutes a gene for the bioconversion of 17OH-progesterone. It was therefore decided to disrupt the GCY1 gene in order to prevent its activity.

Example 4

Construction of the TGY243 Strain

To do this, the TGY212#1 strain was transformed with 3 µg of the plasmid pTG12010#36 linearized with the SphI and EcoRI restriction enzymes. Twenty-seven transformants were selected on a minimum medium supplemented for the auxotrophies of TGY212#1, but containing no uracil.

The colonies were subjected to bioconversion tests in a minimum medium supplemented with galactose as carbon source, because the latter is a known inducer of GCY1. All the TGY243 clones exhibited a capacity to convert 17OH-progesterone to 11-deoxycortisol without, however, producing detectable amounts of 4-pregnene-17α,20α-diol-3-one.

A clone, TGY243#1, was selected in order to introduce in place of the URA3 gene an expression cassette for human P450c21.

Example 5

Construction of the TGY245 Strain

This TGY243#1 strain is transformed with the plasmid YRp7 (1 µg) described by Parent et al., 1985 and with the plasmid pTG12086 linearized with the XhoI enzyme (5 µg).

The pTG12086 transforming fragment contains the coding sequence of GCY1 interrupted by an expression cassette for human P450c21 (TDH3::human P450c21 cDNA:PGK1 terminator).

The colonies which grow in the absence of tryptophan are selected. These 381 colonies are then transferred onto a medium containing tryptophan and 5-fluoroorotate. About ten colonies are then tested in a rich medium of the YPG type supplemented with tryptophan, histidine, leucine and uracil at a concentration of 50 µg/ml.

The strains are allowed to convert 17OH-progesterone at a concentration of 100 µg/ml, starting with an OD 600 nm of 0.1, for 16 hours.

Among these 10 clones, one clone, TGY245#2D, is chosen based on two criteria: its capacity to convert 17OH-progesterone to 11-deoxycortisol and, secondly, the absence of formation of 4-pregnene-17α,20α-diol-3-one, indicating the disruption of GCY1.

Example 6

Construction of the TGY260 Strain

The strain was constructed by transformation of TGY245 with the plasmid pTG12048 which allows overexpression of the ARH1 gene at the LEU2 locus.

The TGY260 strain was constructed from the TGY245 strain which was transformed with the linearized plasmid pTG12048.

This plasmid pTG12048 is an intergenic integration plasmid carrying the LEU2 selection marker. On this plasmid, an expression cassette for the ARH1 gene (Lacour et al., op. cit.) is integrated in the region between the LEU2 gene and the NFS1 gene.

This cassette comprises the CYC1 promoter followed by the ARH1 gene and the PGK1 terminator bordered by NotI restriction sites. This plasmid pTG12048 was linearized with the XhoI and SalI restriction enzymes.

This fragment is used to transform the TGY245 strain using a conventional method of transformation with lithium chloride. The transformant colonies are then selected on a medium containing no leucine. A strain, TGY260, was selected.

The TGY260 strain was deposited with the CNCM [National Collection of Culture in Microorganisms] on Jan. 24, 2001, under the number I-2615.

Example 7

Construction of the CDR07matα Strain

The FY1679-28c strain was transformed with the plasmid pCD62.1, described in Duport et al., 1998 (the technical content of which for constructing the plasmids and obtaining the strains is incorporated into the present application by way of reference), to give the CDR01 strain. This strain is transformed with the plasmid pCD78, also described in Duport et al., and the CA03 strain is obtained.

The ERG5 gene of said CA03 strain is disrupted with a cassette which confers hygromycin resistance, and the CA10 strain is obtained.

This strain is crossed with an FY1679-18b parent strain, and then allowed to sporulate. The spores are isolated according to conventional techniques on a minimum medium supplemented for the auxotrophies, i.e. uracil, tryptophan, leucine and histidine.

The spores are screened based on two criteria, which are nystatin resistance (12 µg/ml in minimum medium) and hygromycin resistance (100-150 µg/ml in rich medium). The spores which are resistant to these two products are then analyzed by gas chromatography for the presence of campesterol as main membrane sterol. The presence of campesterol in the membranes of the strains, combined with an absence of ergosta-5,22-dienol, indicates that the Δ7 reductase is functioning correctly. A CDR07 MATα spore is selected based on the above criteria.

The CDR07 MATα strain was deposited with the CNCM on Jan. 24, 2001, under the number I-2616.

Example 8

Construction of the UCY2 and UCY4 Strains

The TGY260 and CDR07 MATα strains are crossed so as to obtain the SB14 strain. This strain is then allowed to sporulate and the segregating strains YCC4 and YCC5 are obtained (see also below).

These strains are transformed with the plasmid pLIP5 (see below) and give the YCC8 and YCC9 strains, respectively.

These strains are transformed with the plasmid pTG12093, so as to obtain the UCY2 and UCY3 strains, respectively.

The ATF2 gene is inactivated in the UCY2 strain using a plasmid and a selection with G418, and the UCY4 strain is then obtained.

Example 9

Construction of the Plasmids for Transforming the UCY2, UCY3 and UCY4 Strains a) Construction of Plasmid pCV29

Figure 3:
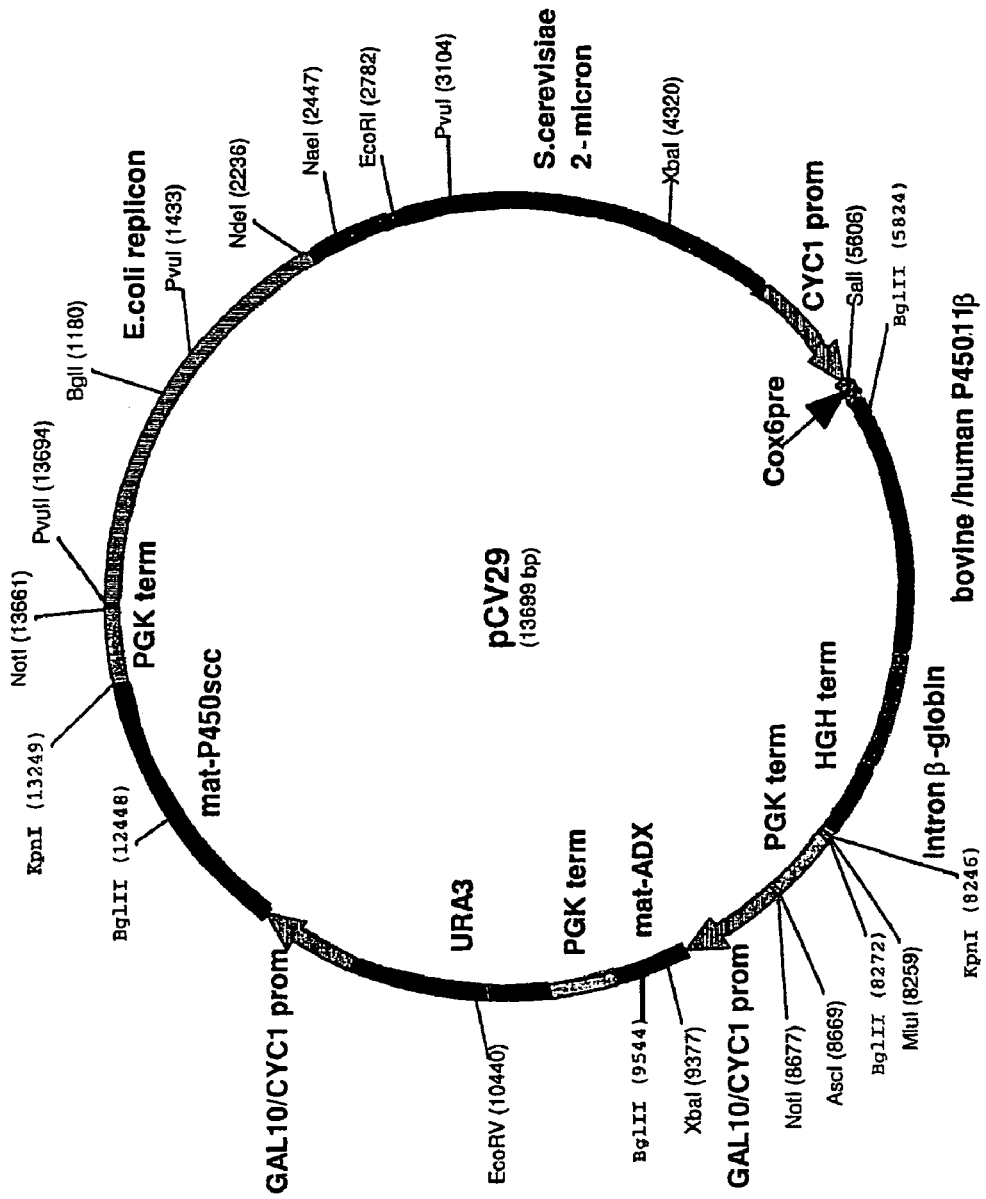
FIG. 3: Map of the plasmid pCV29. PGK term: PGK terminator. GAL10/CYC1 prom: GAL10/CYC1 promoter. HGH term: terminator of the human growth hormone gene. Intron β-globin: intron of the rabbit β-globin gene. CYC1 prom: CYC1 promoter. PGK term: PGK terminator. S. cerevisiae 2-micron: 2-micron origin of replication of S. cerevisiae. Cox6pre: presequence of cytochrome oxidase subunit 6. Bovine/human P450 11β: bovine/human fused cDNA of P45011β. mat-ADX: mature form of ADX with an $NH_2$-terminal methionine. E. coli replicon: E. coli Replicon.

The plasmids pTG10767, pTG10022 and pCD63 were used to construct pCV29 (cf. FIG. 3).

1. Construction of the Plasmid pTG10767

The plasmid pTG10767 is an expression plasmid for P450c11 of human origin. It in fact contains two expression cassettes, one for P450c11 of human origin and the other for adrenodoxin. These two proteins are targeted to be active in the mitochondria of the yeast S. cerevisiae, by the presence of addressing sequences of the cytochrome Cox6p precursor.

This expression cassette for P450c11 of human origin is bordered by two NotI restriction sites which make it possible to transport it in the various vectors described by Degryse et al., 1995. From 5' to 3', it comprises the CYC1 promoter as described in the publication above, and then the modified human P450c11 cDNA as described above and, finally, a noncoding portion from a higher eukaryote.

The human P450c11 cDNA is that described by Chua et al., 1987, with the following modifications.

The portion encoding the signal peptide in the original cDNA was removed up to the BglII restriction site and replaced. This at the same time removes 31 amino acids of the coding sequence of the mature form of the cDNA, to give the following NH$_2$-terminal protein sequence (SEQ ID No. 23):
MLSRAIFRNPVINRTLLRARPGAYHATR-LTKNTFIQSRKYGTRGAAAPKAVLPEAMP RCPGNK-WMRMLQIWREQGYEDLHLEVHQTFQELGPIFRYD LGGAGMVCVMLPEDVEKLQQVDSLHPHRMSLEP WVAYRQH On the preceding line, the part in italics corresponds to the amino acid sequence of the addressing sequence of the precursor of yeast cytochrome oxidase subunit VI (COX6), the part in bold corresponds to the NH$_2$-terminal portion of bovine P450c11 (Dumas et al., 1996). The part underlined corresponds to the beginning of the sequence identical to that published for the human P450111 cDNA (Kawamoto et al., 1990).

The NotI cassette which carries the CYC1 promoter and the chimeric cDNA of P45011β1 also contains a noncoding portion located 3' of the cDNA. This noncoding portion is composed of 3 elements, a noncoding portion originating from the natural cDNA and a noncoding portion originating from the plasmid pCMV4, the sequence of which is deposited at Genbank under the number AF239248 (Andersson et al., 1989). In addition, the only noncoding portions originating from pCMV4, terminator of the human growth hormone gene and the rabbit β-globin gene intron are conserved in the final vector pCV29.

Finally, a DNA fragment carrying NotI restriction sites contains, from 5' to 3', the CYC1 promoter, and a chimeric cDNA framed by SalI and MluI sites containing a portion encoding the presequence of cytochrome oxidase fused to a fragment of bovine P450$_{11β}$ up to the portion corresponding to the restriction site, then the end of the cDNA corresponds to the human P450$_{11β1}$ cDNA. The noncoding portion is made of three of mammalian origin.

This NotI cassette is transferred into the plasmid pTG10359 which is derived from the plasmid pTG10350 (Dumas et al., 1996) digested with the ClaI and PvuII restriction enzymes and religated on itself.

This plasmid pTG10359 also has a unique NotI restriction site. The plasmid pCV29 is a 3-cassette plasmid which contains the expression cassettes for the mature form of ADX and the mature form of P450$_{SCC}$ and a for of human CYP11B1 targeted to mitochondria.

The plasmid pTG10022 is described in the publication by Degryse et al., 1995, incorporated into the present application by way of reference, and contains a 2-micron origin of replication for the yeast S. cerevisiae, and also the elements for cloning in E. coli.

The restriction sites of this plasmid were modified with the oligonucleotides OLIP 174 and OLIP 175 (respectively SEQ ID No. 28 and 29) in order to integrate therein the AscI and PmeI restriction sites.

A double expression cassette of the plasmid pCD63 described by Duport et al., 1998 was introduced at the NotI restriction site of this plasmid. This double expression cassette, contained on a NotI fragment, contains an expression cassette in the mature form of bovine ADX and an expression cassette in the mature form of bovine P450$_{SCC}$ framing a URA3 selection marker. The expression cassette for cytochrome P45011β containing the human P45011β cDNA under the control of the CYC1 promoter and PGK1 terminator was introduced into the unique blunt-ended PmeI site of this plasmid after filling the NotI ends with DNA polymerase Klenow fragment.

One of the plasmids obtained, pCV29, contains three expression cassettes for ADX, P450$_{SCC}$ (both in mature form) and also a form of human P45011β targeted to mitochondria. In addition, this plasmid carries, as a marker, the URA3 gene framed by two expression cassettes.

b) Construction of the Plasmid pCC12

The plasmid pCC12 (cf. FIG. 4) is a replicative yeast plasmid based on the chromosomal origin of replication such as ARS1 and a CEN centromere (there are 16 of them in yeast), both from S. cerevisiae. This plasmid replicates in the form of one or two copies in yeast.

It was constructed from pFL38C2, which is derived from pFL38 (Bonneaud et al., 1991), the content of which is incorporated into the present application by way of reference, in particular the descriptions of the plasmids). An oligonucleotide which contains the recognition sequence of the NotI, PacI and AscI sites (OLIP FL SEQ ID No. 24) was introduced into this plasmid at the HindIII site. The orientation of the polylinker was verified by sequencing. This plasmid carries a URA3 selection marker bordered by BglII sites.

The URA3 gene was replaced with a 2.7 Kb ADE2 gene obtained by PCR amplification on the genome of FY1679-28c using the oligonucleotides 5'ADE2090 (SEQ ID No. 37, CGATTCGGATCCACTAGTAACGCCG-TATCGTGATTAACG) and 3'ADE2089 (SEQ ID No. 38, CCTCAAGGATCCTCCTGACGTAGCGC-TATCCTCGGTTCTG).

To do this, the plasmid pFL38C2 was digested with the BglII enzyme, and the URA3 BglII fragment was replaced with the 2.7 Kb fragment containing the ADE2 gene. The plasmid obtained, pAM1, serves as a basis for constructing the plasmid pCC12.

Construction of the Plasmid from the Plasmid pAM1:

The plasmid pCC12 contains two expression cassettes, one for 3β-HSDH of bovine origin, the other for adrenodoxin reductase, also of bovine origin.

The bovine 3β-HSDH cDNA was recloned by PCR from a bovine adrenal gland cDNA library. The coding sequence with the cDNA published by Zhao et al., 1989, was not modified.

The two oligonucleotides add a SalI site and 4 adenines in front of the ATG, to give the sequence GTCGACAAAAATG (SEQ ID No. 25). The MluI site is located right next to the termination codon of the bovine 3β-HSDH cDNA, to give the sequence: end of the cDNA TGACCTGGAGTGACAAT-GACGCGT (SEQ ID No. 26). The sequence recognized by the MluI enzyme is ACGCGT.

The cDNA is transferred, in the form of a SalI, MluI fragment, into the plasmid pTG10212, to give the plasmid pCC4. This plasmid therefore has a NotI fragment containing the 3β-HSDH cDNA bordered by both a TDH3 promoter and a PGK1 terminator, positioned 5' and 3' respectively. This expression cassette is then transferred into the plasmid pTG12018, and the cassette is thus now bordered in the 5' position by a NotI site and in the 3' position by an AscI site. This fragment is then cloned into the yeast expression plasmid pAM1 in the NotI and AscI sites, to give the plasmid pCC11.

Into the NotI site of this plasmid are inserted the NotI fragment carrying the TEF1 promoter, the cDNA of the mature form of adrenodoxin reductase of bovine origin, and the PGK1 yeast terminator, respectively in this order, originating from the plasmid pTG10361.

This plasmid carries the same cDNA which is described in Dumas et al., 1996 (the content of which is incorporated into the present application by way of reference, in particular the descriptions of the plasmids), except that the addressing sequence of the cytochrome oxidase precursor has been replaced with a methionine codon. The cDNA therefore encodes a mature form of the adrenodoxin reductase cDNA.

Example 10

Construction of the CDR07 Strain

The CDR07 strain was obtained by crossing between the FY1679-18b MAT a strain and the CA10 MAT α strain described by Duport et al., 1998.

These two strains were first of all isolated on a rich medium containing glycerol and then on a medium in a medium containing potassium acetate as described in "Yeast Protocols Methods in Cell and Molecular Biology Edited by Ivor H Evans in 1996. Humana Press Totowa N.J.".

After sporulation, the tetrads were digested with zymolyase 100T for 30 minutes at 37° C. Several cycles of selection were applied in order to obtain a clone which produces campesterol as the major sterol, having lost the other characteristics of CA10.

The spores are first of all selected on a minimum medium containing nystatin with supplements (adenine, leucine, tryptophan, uracil, histidine). The clones resistant to nystatin and auxotrophic for adenine and leucine are then subcultured on rich medium containing adenine and hygromycin (200 μg/ml) in order to detect deletion of the ERG5 gene by the hygromycin resistance gene.

Clones auxotrophic for adenine and leucine (and uracil and tryptophan) and also hygromycin-resistant and nystatin-resistant are analyzed in terms of their sterol profile. Two clones of opposite mating-type signs, producing campesterol as the major sterol, are selected.

They are named CDR07 MAT a and CDR07 MAT α.

Example 11

Construction of the Integration Plasmids pTG12093 and pLIP5 Respectively for the HIS3 and TRP1 loci a) Construction of pLIP5 pLIP5 is a plasmid which can be used for genomic integrations at the TRP1 locus or as a multicopy plasmid in the yeast S. cerevisiae. The basic plasmid which was used to construct this plasmid is the plasmid pFL45S described in Bonneaud et al., 1991 (the content of which is incorporated into the present application by way of reference, in particular the descriptions of the plasmids).

A genomic DNA fragment corresponding to the 5' portion upstream of the TRP1 promoter was first cloned using the oligonucleotides OLIP21 and OLIP22 (respectively SEQ ID No. 30 and 31) to carry out a PCR amplification.

The PCR product was first subcloned into pCR-Script AmpSK(+) (stratagene, La Jolla, Calif., USA). The OLIP21 and OLIP22 ends in fact have a NarI site in the 5' position and a HindIII site in the 3' position. This NarI, HindIII fragment replaced the multiple cloning sites of the plasmid pFL45S described above.

The plasmid obtained, pLIP3, is further modified using the oligonucleotide OLIP20 (SEQ ID No. 32), which is used to replace the unique HindIII site with the unique NotI site. A fragment containing, from 5' to 3', the TEF1 promoter, the cytochrome P-450c17alpha cDNA and then the PGK1 terminator, as described in Degryse et al., 1999 (the content of which is incorporated into the present application by way of reference, in particular the descriptions of the plasmids), is introduced into this NotI site.

The final plasmid pLIP5 can both be used as a multicopy plasmid based on the TRP1 marker, when the 2-micron portion is removed, and it can be used as a plasmid for integration at the TRP1 locus. The cassette is thus integrated 5' of the TRP1 gene.

b) Construction of the Plasmid pTG12093

This plasmid was a plasmid for intergenic integration at the HIS3 locus. This plasmid is constructed from the plasmid pUC-HIS3 described by Duport et al., 1998. The unique XhoI restriction site of this plasmid was transformed into a unique NotI restriction site using a suitable linker while at the same time destroying the XhoI site, to give the plasmid pUC19-HIS3. Into the unique NotI site of this plasmid, [lacuna] a NotI fragment originating from pTG10792. This fragment contains the TDH3 promoter and the cDNA encoding mature bovine ADX fused to the addressing sequence of the precursor of the $COX_6$ cytochrome (of the yeast cytochrome oxidase subunit 6 described in Dumas et al., 1996. The SalI, MulI restriction fragment of plasmid pTG10350 containing the cDNA described previously was transferred into the plasmid pTG10211, so as to form the plasmid pTG10792.

This plasmid therefore has a 1.6 kilobase fragment containing the TDH3 promoter, the cDNA fused between mature bovine ADX and the yeast $COX_6$ presequence, and the PGK1 terminator, from 5' to 3'. This NotI-NotI fragment is inserted into the plasmid pTG12093. HIS3 and the expression cassette are transcribed in the same orientation.

Example 12

Crossing of CDR07 MATα with TGY260 MATa

The SB14 strain (CDR07MATα×TGY260 MATa) is allowed to sporulate in a very depleted medium containing potassium acetate. The various asci are then allowed to grow in a minimum medium containing the following products: uracil, histidine, tryptophan and adenine.

The spores are then selected on a correctly supplemented minimum medium containing from 8 to 12 µg/ml of nystatin. The positive spores are then selected based on the presence of the human P450-c21 cDNA. To do this, the clones are screened in Kappeli medium (M Arreguin de Lorencez, O J Kappeli, 1987) with 2% ethanol (and 0.1% glucose) as carbon source in the presence of 300 mg/ml of 17OH-progesterone.

The bioconversion is incubated for up to 72 hours. The capacity for bioconversion is analyzed by HPLC as described by Dumas et al., 1996 and Degryse et al., 1999 (the contents of which are incorporated into the present application by way of reference, in particular the explanations of the bioconversion studies).

These clones are also analyzed in terms of their sterol profile by gas chromatography as described by Duport et al., 1998 (the content of which is incorporated into the present application by way of reference, in particular the explanations of the bioconversion studies), for the purpose of detecting campesterol and ergosta-5,22-dienol.

Three spores, YCC3, YCC4 and YCC5, are selected on the basis that they produce ergosta-5,22-dienol and campesterol and that they convert 17OH-progesterone to 11-deoxycortisol with a production efficiency of 25, 120 and 42 µg/ml in 72 hours, respectively.

YCC4 and YCC5 are then selected for two further successive transformations with the plasmids pLIP5 and pTG12093 linearized, respectively, with the ApaL1 and EcoRI enzymes. The plasmids pLIP5 and pTG12093 are intergenic expression plasmids for bovine P450c17 and mitochondrial bovine ADX respectively.

pTG12093 is a plasmid for integration into the intergenic region in the position 3' of the HIS3 locus, whereas pLIP5 is a plasmid for integration into the intergenic region in the position 5' of the TRP1 locus. In addition, these two plasmids carry a unique NotI site which allows integration of an expression cassette -containing, in this order; TEF1 promoter, bovine P450c17 cDNA, PGK1 terminator for pLIP5, and in this order; TDH3 promoter, COXVIpre::mat bovine ADX cDNA, PGK1 terminator for pTG12093.

The YCC4 strain is transformed successively with the plasmids pLIP5 and pTG12093 which are linearized (with the ApaLI and EcoRI restriction enzymes).

In the first transformation, the transformant clones are first of all selected on a medium which does not contain tryptophan. The clones which grow in the absence of tryptophan are then selected by PCR with the oligonucleotides C17-3 and C17-5 (respectively SEQ ID No. 33 and SEQ ID No. 34).

A clone, YCC8, is selected for a further transformation with the linearized plasmid pTG12093. In the same way, the clones which grow in the absence of histidine are selected and then the presence of the ADX cDNA is verified by PCR using the oligonucleotides ADX-3 and ADX-5 (respectively SEQ ID No. 35 and SEQ ID No. 36).

A clone, UCY2, is selected; its mating-type sign is MATα.

Example 13

Construction of the UCY4 Strain

The UCY2 strain has a functional ATF2 gene, that is to say most of the pregnenolone produced is transformed to pregnenolone acetate by the ATF2p protein which is a pregnenolone acetyl transferase, the natural function of which in yeast is unknown (Cauet et al., 1999). In addition, this reaction is irreversible and therefore, once it has been produced, the acetyl pregnenolone can no longer be transformed into hydrocortisone. It therefore appears to be important to destroy this activity so as to allow more efficient production of hydrocortisone.

The ATF2 gene was therefore disrupted using a G418 resistance gene. To do this, a disruption plasmid, pAM3kanaC, was constructed, allowing introduction of a G418 resistance marker into the ATF2 gene.

This plasmid was constructed from the plasmid pAM1 (the construction of which was described above), and from the plasmid pTG12002, which is an expression plasmid for the ATF2 gene.

pTG12002 is an expression plasmid for ATF2 based on the plasmid pTG10260 (Degryse et al., 1995) in which the XbaI restriction site of the 2-micron origin of replication has been inactivated. This plasmid therefore comprises an expression cassette for the ATF2 gene (Cauet et al., 1999) comprising the CYC1 promoter, the ATF2 gene (framed by the SalI and MluI restriction sites) and the PGK1 terminator. This cassette was modified by PCR so as to contain the complete ATF2 gene comprising the promoter of the ATF2 gene, the coding sequence of the ATF2 gene, and the terminator of the ATF2 gene, on a KpnI, NotI restriction fragment. This KpnI-NotI fragment is introduced at the KpnI-NotI sites of the plasmid pAM1, to give the plasmid pAM3.

In the plasmid pAM3, the expression cassette for G418 resistance is introduced into the ATF2 gene, causing the inactivation thereof.

To do this, the plasmid pAM3 is digested with the AccI restriction enzyme, and then partially with the SacI restriction enzyme. A band of approximately 7500 bp is purified on a gel. The plasmid pFA6a kanMX4 (Wach et al., Methods in Microbiology Volume 26 Yeast Gene Analysis Chapter 5 PCR-based Gene Targeting in *Saccharomyces cerevisiae*) is digested with SacI and AccI, and the band at 1500 bp is purified on a gel. The two fragments are ligated and then transformed. A plasmid is obtained, pAM3kanaC. pAM3kanaC is digested with PvuII and NotI, and the band at 2215 bp is purified on a gel and then transformed into UCY2, which is plated out on dishes of rich medium containing 130 μg/ml of G418. Approximately 600 clones are subcultured on this medium containing G418, and two clones are resistant to G418. A clone which does not contain the plasmid pAM3 is conserved.

This method of gene activation is well known to those skilled in the art.

The single clone thus obtained is allowed to carry out bioconversion with 100 μg/ml of pregnenolone in Kappeli medium.

After 24 hours, the absence of pregnenolone acetate is verified by extraction and gas chromatography as described in Cauet et al., 1999. This phenomenon indicates that the ATF2 gene responsible for acetylation of pregnenolone has clearly been disrupted and is no longer functional. The strain is named UCY4.

Example 14

Construction of the UCY3 and UCY26 Strains

Screening of the spores obtained by crossing the CDR07 and TGY260 strains gave several strains, including the YCC4 and YCC5 strains. As described above, the YCC4 strain was transformed with a series of 2 plasmids: pLIP5 and pTG12093. A spore, UCY2, was then selected (cf. example 12). In the same way, the YCC5 strain was also transformed with the plasmids pLIP5 and pTG12093 and an additional spore, named UCY3, was obtained. Like UCY2, UCY3 is characterized by the presence and expression of *A. thaliana* Δ7 reductase measured by nystatin resistance and the presence of brassicasterol and campesterol as major sterol of these recombinant yeasts. The presence of the ADX cDNA is verified by PCR using the oligonucleotides ADX-3 and ADX-5 (respectively SEQ ID No. 35 and SEQ ID No. 36), and then by Western blot as described in Dumas et al., 1996, incorporated herein by way of reference as regards the description of this technique.

The activity of progesterone hydroxylation at position 17 and at position 21 is verified by bioconversion of progesterone to 17OH-progesterone and 11-deoxycortisol. To do this, the strain is incubated in the presence of 200 mg/l of progesterone as described in Dumas et al., 1996 and Degryse et al., 1999. UCY3 is capable of producing 11-deoxycortisol from progesterone, indicating the presence of the P450c17 and P450c21 activities. The presence of 4-pregnene-17α,20α-diol-3-one is also detected, indicating that at least one of the two activities encoded by GCY1 or YPR1 is present in the strain. To avoid accumulation of pregnenolone acetate, the pregnenolone acetylation activity encoded by the ATF2 gene was eliminated. With this aim, the plasmid pAM3kanaC (cf. example 13) was used to transform the UCY3 strain. pAM3kanaC is first of all digested with PvuII and NotI, the band at 2215 bp is purified on a gel and is then transformed into UCY3, which is plated on dishes of rich medium containing 130 μg/ml of G418. Colonies resistant to the G418 antibiotic, and which are no longer capable of transforming pregnenolone into pregnenolone acetate, are isolated; a colony, UCY26, is more particularly selected for further transformations and to test its production of hydrocortisone.

Example 15

Construction of the UCY5 Strain

With the aim of having better genetic variability, the UYC2 strain (cf. example 12) was crossed with the TGY245 strain (cf. example 5), and a diploid strain, YSA2-2n, was thus selected. This strain was placed under conditions for the production of asci and 85 asci were dissected (as described in "Yeast Protocols in Molecular Biology Volume 53 p59-67, 1996"). The isolated spores are screened on the basis of their auxotrophic property. Thus, the clones capable of growing in the absence of tryptophan and histidine and requiring adenine are more particularly selected. Expression of Δ7 reductase is verified by making sure that the strain is resistant to nystatin and that campesterol and brassicasterol are present in the membranes of these strains. The latter analysis is carried out by gas chromatography of the total sterols of these strains as described in Duport et al., 1998. In addition, the presence of the cDNAs encoding P450c17 and ADX is verified by PCR using the oligonucleotides C17-3 and C17-5 (respectively SEQ ID No. 33 and SEQ ID No. 34) and the oligonucleotides ADX-3 and ADX-5 (respectively SEQ ID No. 35 and SEQ ID No. 36), respectively. Finally, the functionality of the GCY1 and YPR1 genes in these positive spores is verified in two ways: either by PCR or by the absence of 20-alpha-reductase activity on 17OH-progesterone.

Disruption of the YPR1 gene by the expression cassette for human P450c21 in *S.cerevisiae*, containing the TEF1 promoter, the human P450c21 cDNA and the PGK terminator, is detected by PCR using the pair of oligonucleotides X1TEF1 and X2C21 (respectively SEQ ID No. 47 and SEQ ID No. 48). Disruption of the GCY1 gene by the expression cassette for human P450c21 in *S.cerevisiae*, containing the TDH3 promoter, the human P450c21 cDNA and the PGK terminator, is also detected by PCR using the pair of oligonucleotides X3TDH3 and X2C21 (respectively SEQ ID No. 49 and SEQ ID No. 48).

The disappearance of the two GCY1 and YPR1 activities and the presence of the activity corresponding to the P450c17 and P450c21 activity are finally verified by bioconversion of progesterone to 11-deoxycortisol under the conditions described by Dumas et al., 1996, modified by Degryse et al., 1999. The recombinant yeasts are incubated at 30° C. in the presence of 200 mg/l of progesterone with a cell density of 5 in a culture medium of the Kappeli type containing 2% of galactose or 2% of glucose as carbon source, in a volume of 10 ml. After incubation for 48 hours, the culture medium of these yeasts is extracted as described previously and the amount of 17OH-progesterone and 11-deoxycortisol produced in particular are measured by HPLC. The spore selected no longer produces a detectable amount of 4-pregnene-17α,20α-diol-3-one, but produces 17αH-progesterone and 11-deoxycortisol using the two carbon sources. The clone chosen produces the largest amount of 1-deoxycortisol.

A strain which satisfies positively all these criteria is more particularly selected for further transformations; this strain is named UCY5.

Example 16

Construction of the Plasmids pFM10 and pTG10897 a) Construction of the Plasmid pFM10

The plasmid pFM10 is a vector which allows the simultaneous expression of 4 proteins in yeast. It contains no origin of replication for *E. coli* nor an ampicillin resistance gene; this plasmid cannot replicate in *E. coli*. It is obtained by recombination in yeast of two plasmids: pFM7 and pCB12. These plasmids, unlike the plasmid pFM10, both replicate in *E. coli* since they possess the *E. coli* replicon. The plasmid pFM7 also replicates in *S.cerevisiae*, since it also comprises the 2-micron origin of replication of the yeast *S.cerevisiae*. These two plasmids also have the R1 and R2 sequences (respectively SEQ ID No. 39 and SEQ ID No. 40) bordering the expression cassettes and also the selection markers. The R1 and R2 sequences come from the *A. thaliana* photochlorophyllide oxidoreductase gene and are each approximately 300 base pairs in size.

The two sequences R1 and R2 are cloned in reverse orientation into the plasmids pFM7 and pCB12. Thus, between the R1 and R2 sequences, the pFM7 plasmid contains, in the following order: the 2-micron origin of replication contained in the 2-micron fragment (fragment bordered by the EcoRI restriction sites, as described by Urban et al., 1994), a fragment bordered by NotL sites originating from the plasmid pCD63 described in Duport et al., 1998 containing two expression cassettes for the mature form of $P450_{SCC}$ and the mature form of ADX separated by the functional yeast URA3 gene, and then the R2 sequence. Similarly, the plasmid pCB12 contains the R1 and R2 sequences, but they are cloned in the direction opposite to that of the plasmid pFM7. Thus, between the R2 and R1 sequences, there is the expression cassette for $P450_{11\beta}$, the ADE2 selection marker and the expression cassette for 3β-HSD of bovine origin. The expression cassette for $P450_{11\beta}$ comes from the plasmid pCV29 and contains the CYC1 promoter, a hybrid cDNA encoding $P450_{11\beta}$ and a PGK terminator. The ADE2 gene comes from the plasmid pAM1; it is the BglII-BglII fragment. Similarly, the expression cassette for bovine 3β-HSD, i.e. the TDH3 promoter, the bovine 3β-HSD cDNA and the PGK terminator, comes from the plasmid pCC12; it is the ClaI-AscI fragment.

b) Construction of the Plasmid pTG10897

The coding sequence of the ATF2 gene is amplified by PCR using two 20mer oligonucleotides corresponding respectively to the 5' and 3' portion of the coding sequence of the ATF2 gene (and also comprising the cloning sites) and using as matrix genomic DNA from the FY 1679-28c strain. This PCR product is then digested with the ClaI and HindIII enzymes and is cloned between the ClaI and HindIII sites of the plasmid pTG10031 [Degryse, 1995 #102], to give the plasmid pTG10885. This plasmid is used as a basis for the construction of a plasmid for disrupting the ATF2 gene. The sequence of the URA3 gene was amplified from genomic DNA of the TGY156 strain (described in Cauet et al., 1999 and incorporated herein by way of reference); this strain in fact has an ATF2 gene interrupted by the URA3 gene. The oligonucleotides OTG10842 (SEQ ID No. 41) and OTG10841 (SEQ ID No. 42) were therefore used for the amplification on a matrix of genomic DNA from the TGY156 strain, and the amplification product was used as an initiator of recombination with the plasmid pTG10885 digested with the BstXI and StuI restriction enzymes.

The plasmid pTG10897 containing the coding sequence of the ATF2 gene interrupted by the URA3 gene is thus obtained. Specifically, the functional URA3 gene is located between 509 nucleotides of the 5' portion of the coding sequence of ATF2 and 444 nucelotides of the 3' portion of this coding sequence.

Example 17

Construction of the UCY6, UCY16, UCY16-pFM10, UCY19, UCY20, UCY24, UCY25 and UCY27 Strains A series of new strains was constructed, based on the UCY5 strain, with the aim of improving the production of steroid of interest. Specifically, the UCY5 strain does not express adrenodoxin reductase, which is an essential component of the reaction for side chain cleavage by $P450_{SCC}$. Furthermore, as was described previously, the ATF2 gene encodes an acetyl transferase which uses pregnenolone as substrate, and disruption thereof makes it possible to eliminate this parasitic acetylation reaction and to thus increase the yield of steroid of interest. Finally, the exogenous biosynthetic pathway uses the endogenous ARH1p activity, the latter being essential to yeast survival. However, this mitochondrial activity, which replaces mammalian adrenodoxin reductase, might be limiting in the strains producing hydrocortisone. A strain having certain modifications making it possible to considerably increase the yield of production of steroid of interest was therefore constructed based on the UCY5 strain. Thus, this strain lacks ATF2 activity, overproduces the adrenodoxin reductase protein and also overproduces the ARH1 protein.

In order to allow ADR to be expressed in the UCY5 strain, the latter was transformed with the vector pTG10925 (cf. example 2 f), which, when it is transformed in yeast in linear form, allows integration at the LEU2 locus and expression of ADR under the control of the TEF1 promoter. The expression of ADR was verified by Western blotting as described in Dumas et al., 1996. A clone expressing ADR, and named UCY6, was more particularly used for the subsequent transformations.

With the aim of eliminating the parasitic acetylation reaction transforming pregnenolone into pregnenolone acetate catalyzed by the ATF2 enzyme, the ATF2 gene encoding this enzyme was disrupted. Specifically, this gene was interrupted by the URA3 marker; to do this, the NotI fragment of the plasmid pTG10897, which contains the sequence of the ATF2 gene interrupted by the functional yeast URA3 gene, was used. This fragment is used to transform the UCY6 strain. The colonies capable of growing in the absence of uracil are selected, and then the capacity of these clones to transform pregnenolone into pregnenolone acetate is measured as described by Cauet et al., 1999. A clone capable of growing in the absence of uracil and incapable of transforming pregnenolone into pregnenolone acetate is more particularly isolated. This clone is called UCY16.

Figure 5:
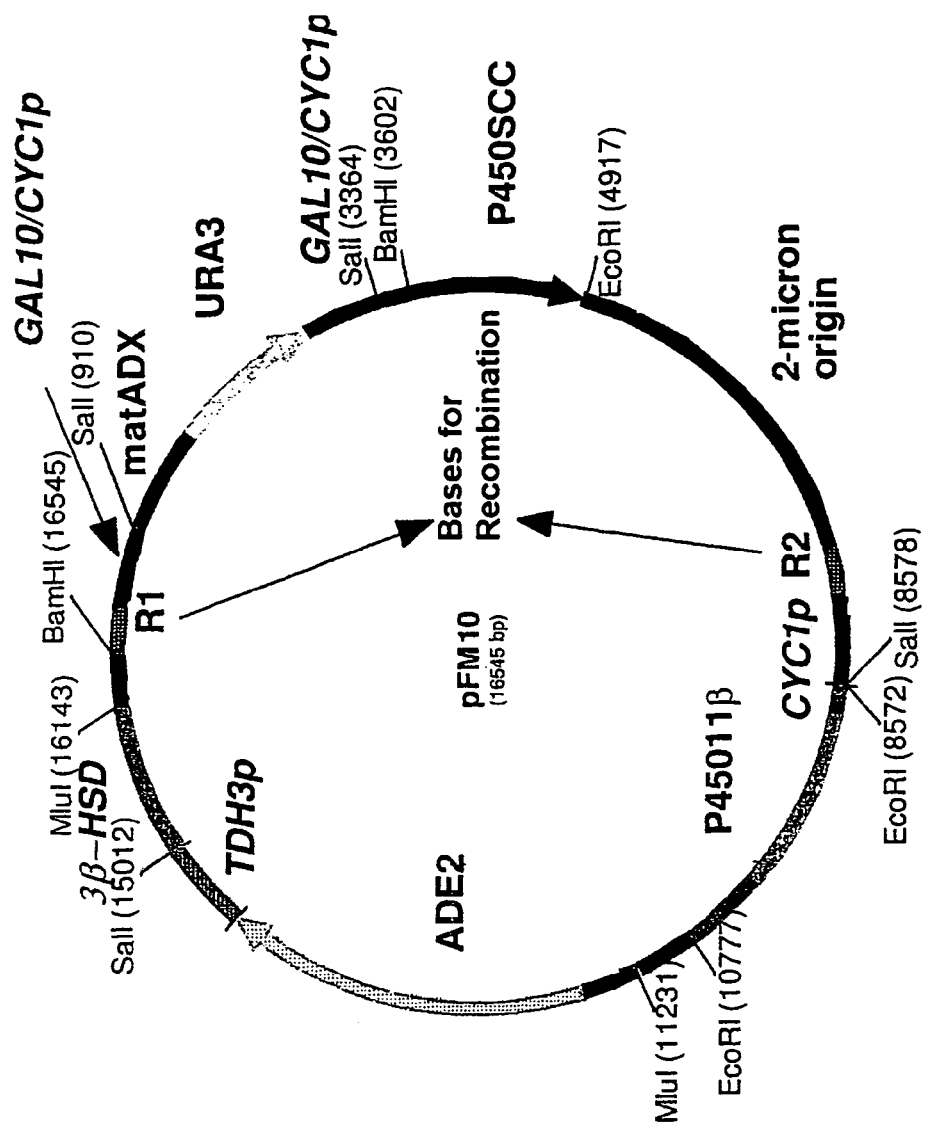
FIG. 5: Map of plasmid pFM10. $CYC1_p$: CYC1 promoter. P45011β: bovine/human fused cDNA of P45011β. ADE2: yeast ADE2 gene. TDH3p: TDH3 promoter. 3β-HSD: 3β-hydroxysteroid dehydrogenase cDNA. R1: base for recombination, the sequence of which is given in SEQ ID No. 39. GAL10/CYC1p: GAL10/CYC1 promoter. matADX: cDNA encoding the mature form of ADX. URA3: yeast URA3 gene. $P450_{SCC}$: cDNA encoding the mature form of $P450_{SCC}$ (CYP11A1). 2-micron origin: 2-micron origin of replication of S. cerevisiae. R2: base for recombination, the sequence of which is given in SEQ ID No. 40.

Since this strain cannot be transformed with plasmids carrying only the URA3 marker, two new plasmids were constructed: the plasmids pCB12 and pFM7. These two plasmids, when they are recombined together, make it possible to obtain the plasmid pFM10 based on the URA3 and/or ADE2 markers (cf. above and FIG. 5). Thus, to obtain the plasmid pFM10, the plasmid pFM7 is linearized with the AatII restriction enzyme and the corresponding DNA fragment is isolated on a gel. The plasmid pCB12 is, for its part, digested with BamH1 and the 9300 base pair band is isolated according to conventional molecular biology techniques. Approximately 5 µg of the pCB12 and pFM7 fragments are mixed and are used to transform the UCY16 strain. Some UCY16-pFM10 clones, capable of growing in minimum medium (without uracil and amino acids), are isolated and the corresponding strains are tested for their level of steroid production according to the protocol described below.

Alternatively, and with the aim of being able to subsequently use the plasmids of the pCV29 type based on a URA3 marker, the disruption of the ATF2 gene in the UCY6 strain was also obtained by transforming this strain with the linearized plasmid pAM3kanaC (cf. example 13). The G418-resistant colonies are then tested for the absence or presence of pregnenolone acetyl transferase activity as described by Cauet et al., 1999. A G418-resistant colony no longer having pregnenolone acetyl transferase activity is more particularly selected. This strain is called UCY24.

With the aim of increasing the ARH1 activity in a strain containing an exogenous pathway for production of hydrocortisone, the UCY5 strain was transformed with the plasmids pTG12048 or pTG12050 linearized beforehand with XhoI and SapI respectively. The plasmid pTG12048 which was described above allows overexpression of the ARH1 gene at the LEU2 locus under the control of the CYC1 promoter. The plasmid pTG12050 differs from the plasmid pTG12048 only in that the CYC1 promoter controlling expression of the ARH1 gene has been replaced with the TEF1 promoter as described in Degryse et al., 1995 and Dumas et al., 1996. UCY5 was transformed with linearized pTG12048 or pTG12050. In each of the two cases, the colonies capable of growing in the absence of leucine were selected. In addition, the presence of the expression cassettes for the ARH1 gene was verified by PCR. Specifically, two pairs of oligonucleotides make it possible to verify the presence of an additional copy of the ARH1 gene (under the control of the CYC1 or TEF1 promoter). First, the pair arh1D (SEQ ID No. 43) and nfs1R (SEQ ID No. 44) makes it possible to verify the presence of the junction between the ARH1 gene and the NFS1 gene. Secondly, the pair leu2D (SEQ ID No. 45) and arh1R (SEQ ID No. 46) makes it possible to verify the junction between the LEU2 gene and the ARH1 gene.

Figure 2:
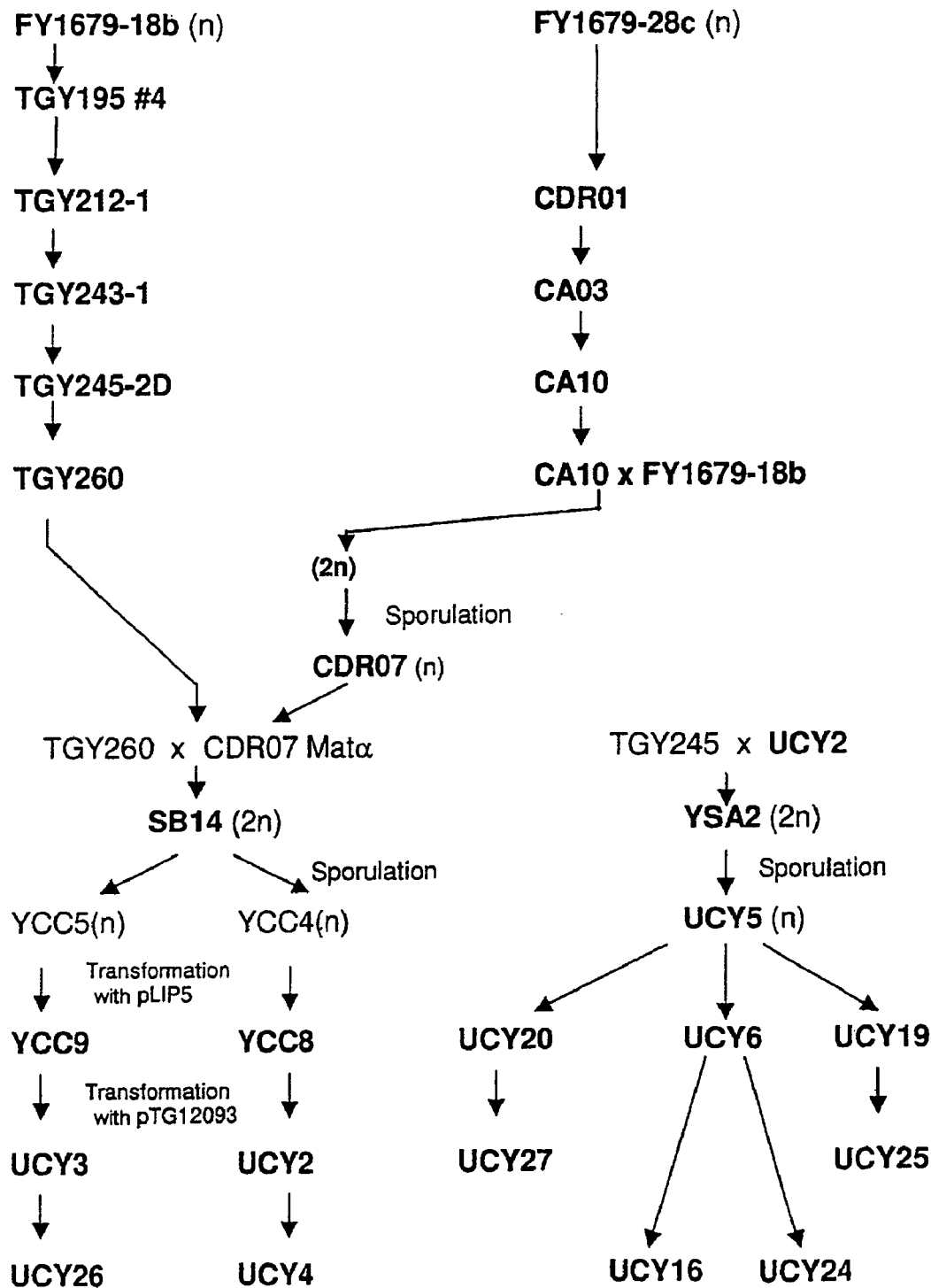
FIG. 2: Diagrammatic representation of construction of yeast strains exemplified according to the invention.

Besides the presence of the expression cassettes for the ARH1 gene encoding the ARH1 activity, the expression of the ARH1p protein was also tested in the clones obtained. It is not, however, easy to detect overexpression of ARH1p. This is due to the natural presence of the ARH1p protein at a low level in S. cerevisiae strains. Western blotting experiments carried out as described in Dumas et al., 1996 make it possible, however, to confirm the increase in the amount of ARH1p. In addition to the Western blotting experiments which prove to be tricky, the presence of an increased amount of ARH1p can be verified with experiments consisting of cytochrome c reduction or of 11beta-hydroxylation of 11-dioxycortisol, which experiments are reconstituted in vitro with purified mitochondria from recombinant yeasts as described in Lacour et al., 1998 and Dumas et al., 1996, respectively. Two clones, UCY19 and UCY20, respectively transformed with pTG12048 and pTG12050 and overexpressing ARH1, are more particularly selected. The ATF2 gene was then disrupted in these strains as described above. Briefly, the plasmid pAM3kanaC was linearized and then used to transform the UCY19 and UCY20 strains. The clones were then selected on the basis of their property of G418 resistance and the absence of pregnenolone acetyl transferase activity as described by Cauet et al., 1999. Two clones derived from UCY19 and UCY20 are more particularly selected. They are, respectively, the UCY25 and UCY27 strains (cf. FIG. 2).

Example 18

Production of Steroids by the Strains According to the Invention a) Transformation of UCY2 and UCY4 with pCV29 and pCC12

Figure 4:
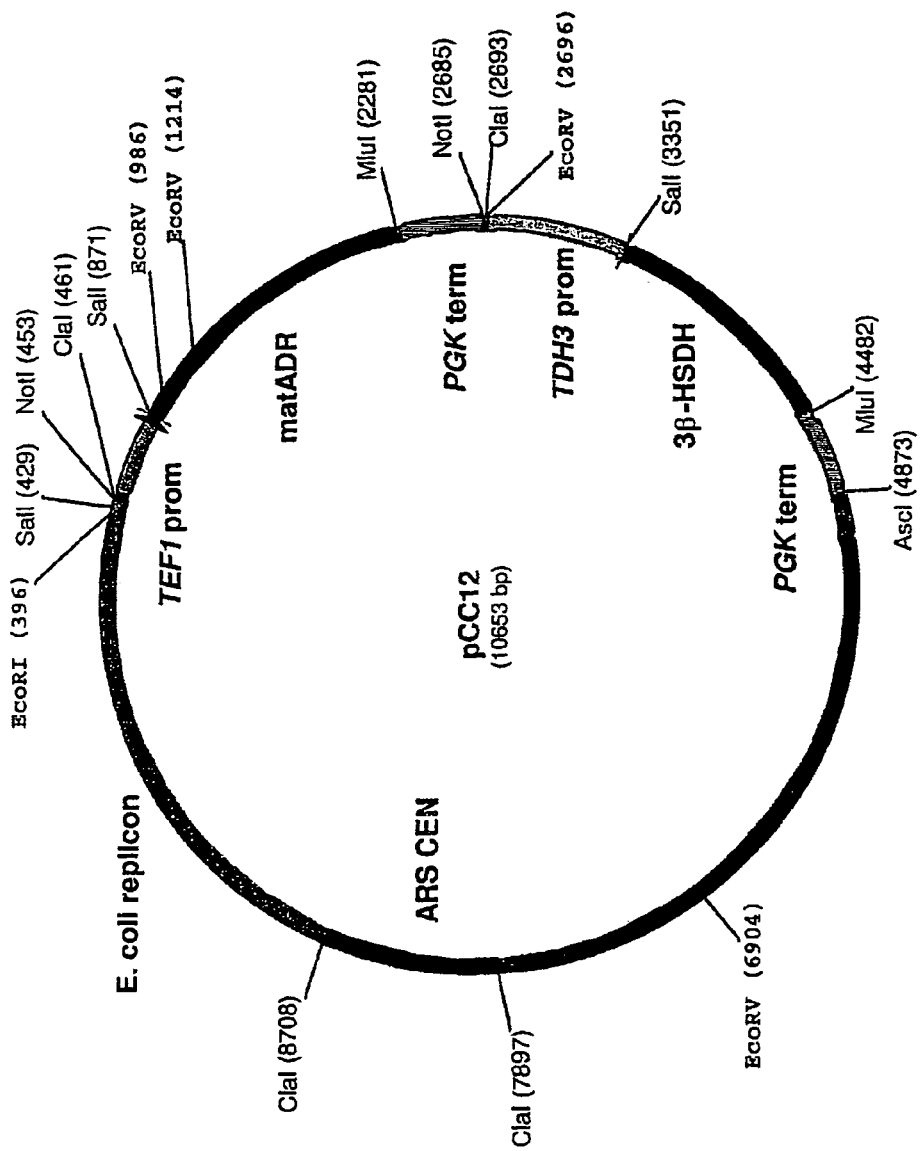
FIG. 4: Map of the plasmid pCC12. CYC1 prom: CYC1 promoter. PGK term: PGK terminator. ARS CEN: S. cerevisiae chromosomal origin of replication. E. coli replicon: E. coli Replicon. TDH3 prom: TDH3 promoter. 3β-HSDH: 3β-hydroxysteroid dehydrogenase cDNA. matADR: mature form of ADR preceded by a methionine.

The UCY2 and UCY4 strains were transformed with the two plasmids pCV29 and pCC12, described above, the structures of which are recalled below and in FIGS. 3 and 4.

The plasmid pCV29 carries a 2-micron origin of replication for replication in yeast. In addition, this plasmid carries 3 expression cassettes respectively for the hybrid human/bovine $P450_{11\beta}$ targeted to mitochondria as described above, and the mature forms (with a methionine at the $NH_2$-terminal end) of adrenodoxin and of P450scc. The expression of these three proteins is under the control of the CYC1 promoter (P45011β) and the GAL10/CYC1 promoter (ADX and $P450_{SCC}$ in mature form).

The plasmid pCC12 is a low copy plasmid which carries an expression cassette for the mature form of bovine adrenodoxin reductase under the control of the TEF1 promoter and also an expression cassette for bovine 3β-HSD under the control of the TDH3 promoter.

These strains are allowed to grow under conventional fermentation conditions in Kappeli medium with glucose as carbon source. At the end of fermentation (180 h), the steroids are extracted as described previously and characterized by high pressure liquid chromatography.

The identity of the products was verified by gas chromatography, and by reverse-phase and liquid-phase high pressure chromatography, possibly coupled with mass spectrometry and nuclear magnetic resonance (cf. table 1).

TABLE 1

Review of the steroids obtained (results expressed in mg/l)

| Strains | Pregnenolone acetate | Progesterone | 4-Pregnene-17α-20α-diol-3-one | Not identified | Corticosterone | Hydrocortisone |
|---|---|---|---|---|---|---|
| UCY2/pCV29 + pCC12 | 18 | 7 | 5 | 5 | 12 | 15 |
| UCY4/pCV29 + pCC12 | 0 | 30 | 44 | 24 | 23 | 80 | b) Transformation of the UCY24, UCY25, UCY26 and UCY27 Strains with pCV29 and pCC12 and Transformation of the UCY16 Strain with pFM10

These strains have many modifications and prove to be difficult to transform. Consequently, a protocol based on preparing spheroplasts was used for these transformations, as described by Burgers et al., 1987. UCY16 was transformed according to this protocol with the plasmids pFM7 and pCB12, the latter ones giving the plasmid pMF10 by recombination in vivo in yeast. As described above, the plasmid pFM10 is a multicopy yeast plasmid which does not contain any bacterial sequences and allows the expression of 4 heterologous proteins. These four proteins are as seen above; a chimeric form of cytochrome $P450_{11\beta}$, bovine 3β-HSD, mature ADX and mature cytochrome P450sc. The corresponding cDNAs are placed, respectively, under the control of the CYC1, TDH3, GAL10/CYC1 and GAL10/CYC1 promoters. The transformants are selected on a minimum medium with nothing added. The selection is carried out only on the basis of the ADE2 marker (growth in the absence of adenine); the presence of a functional URA3 gene in the genome, and which is used to inactivate the ATF2 gene, does not make it possible to select on the basis of the URA3 gene. It is therefore necessary to screen several colonies in order to be sure of having a plasmid pFM10 which is functional in the UCY16 strain.

The UCY24, UCY25, UCY26 and UCY27 strains were transformed with the plasmids pCV29 and pCC12 according to the same protocol for preparing spheroplasts. As described above, the plasmid pCV29 is a multicopy plasmid for shuttling between *E. coli* and *S.cerevisiae*. It allows the expression of cytochrome $P450_{11\beta}$, mature ADX and cytochrome $P450_{SCC}$ respectively under the control of the CYC1, GAL10/CYC1 and GAL10/CYC1 promoters (cf. FIG. 3). The pCC12 plasmid is a single copy yeast plasmid which allows expression of mature bovine ADR and bovine 3β-HSD under the control of the TEF1 and TDH3 promoters, respectively (cf. FIG. 4).

All these strains are allowed to grow in an Erlenmeyer flask (100 ml volume and containing 30 ml of culture medium) under conventional fermentation conditions in Kappeli medium with 2% of ethanol and 0.1% of glucose as carbon source. After culturing for 168 hours, 500 µl of culture medium (cells+medium) are extracted twice with 4 ml of dichloroethane. The organic phase is pooled and then separated into two to be dried under a stream of nitrogen. The dry extract is resuspended in 100 µl of an acetonitrile/water (50/50, volume/volume) mixture or 100 µl of dichloroethane. The extracts resuspended in the acetonitrile/water mixture are processed by HPLC; this allows analysis of the composition of various steroids (hydrocortisone, cortexolone, corticosterone, 17OH-progesterone, 4-pregnene-17α,20α-diol-3-one) as described in Valvo et al., 1994. The extracts resuspended in dichloroethane are analyzed by gas chromatography as described in Duport et al., 1998, the latter analysis making it possible to measure the amount pregnenolone and of progesterone in the samples. For each of the strains transformed, the steroid productivity of about ten clones is thus measured. The results presented below give the results of the best of the ten clones tested for each of the UCY24, UCY25, UCY26 and UCY27 strains transformed with pCV29 and pCC12, and the UCY16 strain transformed with pFM10.

TABLE 2

Review of the steroids obtained (results expressed in mg/l except for the final line: results expressed as percentage of total steroids)

|  | UCY24 pCV29 + pCC12 | UCY25 pCV29 + pCC12 | UCY26 pCV29 + pCC12 | UCY27 pCV29 + pCC12 | UCY16 pFM10 | UCY4 pCV29 + pCC12 |
|---|---|---|---|---|---|---|
| 17OH-Progesterone | 0.6 | 0.6 | 1.0 | 0.6 | 0.5 | 0.2 |
| Deoxycorticosterone | 0.5 | 0.0 | 0.2 | 0.3 | 1 | 0.0 |
| Cortexolone | 4.5 | 2.7 | 2.1 | 2.0 | 7.6 | 0.7 |
| 4-Pregnene-17α, 20α-diol-3-one | 0.0 | 0.0 | 0.0 | 0.0 | 0.0 | 4.5 |
| Corticosterone | 7.5 | 10.8 | 7.5 | 9.0 | 8.9 | 3.4 |
| Hydrocortisone | 17.7 | 29.2 | 22.3 | 24.7 | 15.8 | 12.3 |
| Total steroids | 30.8 | 43.3 | 33.1 | 36.6 | 33.8 | 21.2 |
| % Hydrocortisone | 57 | 67 | 67 | 67 | 47 | 58 |

NB: Neither pregnenolone nor pregnenolone acetate is detected in the culture medium of these strains The UCY16 pFM10, UCY24 pCV29+pCC12, UCY25 pCV29+pCC12, UCY26 pCV29+pCC12 and UCY27 pCV29+pCC12 strains presented above are therefore capable of producing amounts of hydrocortisone greater than those produced by the UCY4/pCV29+pCC12 strain. The total amount of steroids thus increases from 21.2 µg/ml in the UCY4/pCV29+pCC12 strain to 43.3 µg/ml in the UCY25 pCV29+pCC12 strain, whereas the amount of hydrocortisone increases from 12.3 µg/ml to 29.2 µg/ml, respectively. In addition, in these examples, hydrocortisone represents up to approximately 70% of the total steroids. A large increase in the amount and the quality of the hydrocortisone produced is therefore observed since none of these strains produces the 4-pregnene-17,20-diol-3-one contaminant. The latter, particularly advantageous characteristic is due to the absence of the proteins encoded by the GCY1 and/or YPR1 genes which are responsible for the reaction of reduction of the ketone at position 20.

It is also interesting to note that, unexpectedly, the controlled overproduction of ARH1p under the control of the CYC1 promoter significantly increases the amount of total steroids produced and also the production of hydrocortisone (cf. UCY24 pCV29+pCC12 versus UCY25 pCV29+pCC12). However, this expression should not be too great to obtain the desired effect. Thus, if expression of the ARH1 protein at a level greater than a physiological level is desirable, care should be taken not to overexpress this protein too strongly, otherwise there is a risk of losing this increase in production of steroids. Thus, the TEF1 promoter which is acknowledged to be much stronger than CYC1 (Nacken et al., 1996) gives unsatisfactory results (cf. UCY25 pCV29+pCC12 versus UCY27 pCV29+pCC12). In conclusion, the UCY25/ pCV29+pCC12 strain has an estimated potential to produce 200 mg/l of hydrocortisone in a fermenter with a single major contaminant (corticosterone).

c) Example of Large-volume Production of the Strains According to the Invention

Two of the above strains were allowed to grow in a large-volume fermenter in Kappeli medium according to techniques well known to those skilled in the art (cf. D. Risenberg et al., 1999, for example). The culturing technique used is fed-batch with concentrated medium. The fermenter, having a total volume of 15 liters, contains 6 liters of medium at the start. The continuous addition of 4 liters of additional concentrated medium during the fermentation and also of pH-correcting liquids and the continuous addition of ethanol brings the final volume to approximately 11.5 liters at the end of culturing. The UCY4 pCV29+pCC12 and UCY16 pFM10 strains were thus cultured for 180 h and an increased production in hydrocortisone could thus be obtained (cf. table 3). The results which could be envisioned for the UCY24 pCV29+pCC12, UCY25 pCV29+pCC12, UCY26 pCV29+ pCC12 and UCY27 pCV29+pCC12 strains were extrapolated from these results (cf. table 3).

TABLE 3

Production of hydrocortisone by various clones obtained according to the invention (results in mg/l)

| Strains | Hydrocortisone in mg/l |
|---|---|
| UCY4 pCV29 + pCC12 | 80 |
| UCY16 pFM10 | 110 |
| UCY24 pCV29 + pCC12 | 123* |
| UCY25 pCV29 + pCC12 | 203* |
| UCY26 pCV29 + pCC12 | 155* |
| UCY27 pCV29 + pCC12 | 172* |

*These results were obtained by extrapolating the results obtained in a large-volume fermenter with the UCY4 pCV29 + pCC12 and UCY16 pFM10 strains.

Deposition of Biological Material

The following organisms were deposited on Jan. 24, 2001, at the Collection Nationale de Cultures de Microorganismes (CNCM) [National Collection of Cultures and Microorganisms], 25 rue du Docteur Roux, 75724 Paris Cedex 15, France, according to the provisions of the Treaty of Budapest.

| CDR07 MATα strain | Accession number I-2616 |
|---|---|
| TGY260 strain | Accession number I-2615 |

List of the Strains Described in the Present Application

Fy1679-18b=(n)MATa ura3-52 trp1-Δ63 leu2-Δ1 his3-Δ200 fen1 GAL fen$^S$ ura$^-$ trp$^-$ leu$^-$ his$^-$
Fy1679-28c=(n)MATα ura3-52 trp1-Δ63 leu2-Δ1 his3-Δ200 fen1 GAL fens ura$^-$ trp$^-$ leu$^-$ his$^-$
TGY195#4=Fy679-18b ypr1::URA3
TGY212-1=Fy1679-18b ypr1::TEF1$_p$::P450c21 [5x?] ura$^-$ trp$^-$ leu$^-$ his$^-$
TGY243-1=TGY212-1 gcy1::URA3 trp$^-$ leu$^-$ his$^-$
TGY245-2D=TGY243-1 gcy1::TDH3$_p$::P450c21 ura$^-$ trp$^-$ leu$^-$ his$^-$
TGY260-A=TGY245-2D LEU2::CYC1$_p$::ARH1 ura$^-$ trp$^-$ his$^-$
CDR01=Fy1679-18b MATαLEU2::'b-mat ADR' ura$^-$ trp$^-$ his$^-$
CDR07 MATα=MATαade2::GAL10/CYC1$_p$::Δ$^7$ ura$^-$ trp$^-$ leu$^-$ his$^-$ ade$^-$ (spore of CA10×Fy1679-28c)
CDR07 MATα=MATα ade2::GAL10/CYC1$_p$::Δ$^7$ ura$^-$ trp$^-$ leu$^-$ his$^-$ ade$^-$ (spore of CA10×Fy1679-28c)
CA03=CDR01 ade2::GAL10/CYC1$_p$::Δ$^7$ ura$^-$ trp$^-$ ade$^-$ his$^-$, resistant to nystatin (Duport et al., 1998)
CA10=CA03 erg5::PGK1$_p$::hygro$^R$ ura$^-$ trp$^-$ ade$^-$ his$^-$, resistant to nystatin and hygromycin (Duport et al., 1998)
SB14 (2n)=TGY260-A×CDR07 Matα
YCC4=(n) MATαade2::GAL10/CYC1$_p$::Δ$^7$, LEU2:: CYC1$_p$::ARH1, ypr1::TEF1$_p$::P450c21, ERG5, fen1 (?), ura$^-$ trp$^-$ ade$^-$ his$^{-1}$, resistant to nystatin, (spore of SB14)
YCC8=YCC4 transformed with pLIP5 (TRP1::TEF1$_p$:: P450c17:: PGK1$_t$), ura$^-$ ade$^-$ his$^-$, resistant to nystatin
UCY2=YCC8. transformed with pTG12093 (HIS3::TDH3$_p$: CoxVI$_{pre}$::matADX::PGK1$_t$):HIS3::TDH3$_p$::CoxVI$_{pre}$:: matADX::PGK1$_t$, ERG5, fen1 (?), ura$^-$ ade$^-$, resistant to nystatin
UCY4=UCY2 atf2-Δ::G418$^R$ ura$^-$ ade$^-$, resistant to nystatin and to G418.
YCC5=(n) MATa ade2::GAL10/CYC1$_p$::A7Reductase, LEU2::CYC1$_p$::ARH1, gcy1::TDH3$_p$::P450c21, ERG5, fen1(?), ura$^-$ trp$^-$ ade$^-$ his$^-$, (resistance to nystatin, spore of SB14).
YCC9=YCC5 transformed with pLIP5 (TRP1::TEF1p:: P450c17::PGK1$_t$), ura$^-$ ade$^-$ his$^-$, resistant to nystatin.
UCY3=YCC9 transformed with pTG12093 (HIS3::TDH3$_p$:: CoxVI$_{pre}$::matADX::PGK1$_t$):HIS3::TDH3$_p$::CoxVI$_{pre}$:: matADX::PGK1$_t$, ERG5, fen1 (?), ura$^-$ ade, (resistant to nystatin).
UCY26$^-$ UCY3 atf2-Δ::G418R ura$^-$ ade$^-$, (resistant to nystatin and to G418).
YSA2 (2n)=TGY245-2D×UCY2.
UCY5=(n) MATα ade2::GAL10/CYC1$_p$::Δ7Reductase, LEU2::CYC1$_p$::ARH1, ypr1::TEF1$_p$::P450c21, ERG5, gcy1::TDH3$_p$::P450c21 fen1(?), ura$^-$ trp$^-$ his$^-$, resistant to nystatin (spore of YSA2).
UCY6=UCY5 LEU2::TEF1::matADR::PGK1$_t$.
UCY16=UCY6, atf2::URA3::atf2.
UCY19=UCY5, LEU2::CYC1::ARH1.
UCY20=UCY5, LEU2:: TEF1:: ARH1.
UCY25=UCY19, atf2-Δ::G418R (resistant to nystatin and to G418).
UCY27=UCY20, atf2-Δ::G418R (resistant to nystatin and to G418).
UCY24=UCY6, atf2-Δ::G418R (resistant to nystatin and to G418).

BIBLIOGRAPHY

Andersson S. et al., Cloning, structure, and expression of the mitochondrial cytochrome P-450 sterol 26-hydroxylase, a bile acid biosynthetic enzyme. J. Biol, Chem. 1989. 264 (14): p. 8222-8229.

Arreguin de Lorencez M and Kappeli C J, Regulation of gluconeogenic enzymes during the cell cycle of *Saccharomyces cerevisiae* growing in a chemostat. Gen Microbiol, 1987. 133 (Pt 9): p. 2517-22.

Bonneaud N. et al., A family of low and high copy replicative, integrative and single-stranded *S. cerevisiae/E. coli* shuttle vectors. Yeast, 1991 Aug-Sep; 7(6): p. 609-15

Burgers P. M. and Percival K. J., Transformation of yeast spheroplasts without cell fusion. Anal Biochem, 1987. 163 (2): p. 391-7.

Cauet G. et al., Pregnenolone esterification in *Saccharomyces cerevisiae*. A potential detoxification mechanism. Eur J Biochem, 1999. 261(1): p. 317-24.

Chua S C. et al., Cloning of cDNA encoding steroid 11 beta-hydroxylase (P450c11). Proc Natl Acad Sci USA, 1987. Oct; 84(20): p. 7193-7.

Degryse E. et al., In vivo cloning by homologous recombination in yeast using a two-plasmid-based system. Yeast, 1995. 11(7): p. 629-40.

Degryse E., In vivo intermolecular recombination in *Escherichia coli*: application to plasmid constructions. Gene, 1996. 170(1): p. 45-50.

Degryse E. et al., Pregnenolone metabolized to 17alpha-hydroxyprogesterone in yeast: biochemical analysis of a metabolic pathway. J Steroid Biochem Mol Biol, 1999. 71(5-6): p. 239-46.

Dumas B. et al., 11 beta-hydroxylase activity in recombinant yeast mitochondria. In vivo conversion of 11-deoxycortisol to hydrocortisone. Eur J Biochem, 1996. 238(2): p. 495-504.

Duport C. et al., Self-sufficient biosynthesis of pregnenolone and progesterone in engineered yeast. Nat Biotechnol, 1998. 16(2): p. 186-9.

Hu M C. and Chung B C., Expression of human 21-hydroxylase (P450c21) in bacterial and mammalian cells: a system to characterize normal and mutant enzymes. Mol Endocrinol., 1990. 4(6): p. 893-8.

Kawamoto T. et al., Cloning of cDNA and genomic DNA for human cytochrome P-450 11 beta. FEBS Lett, 1990. 269 (2): p. 345-9.

Kuronen P. et al., Reversed-phase liquid chromatographic separation and simultaneous profiling of steroidal glycoalkaloids and their aglycones. J Chromatogr A, 1999. 863(1): p. 25-35.

Lacour T., T. Achstetter, and B. Dumas, Characterization of recombinant adrenodoxin reductase homologue (Arh1p) from yeast. Implication in in vitro cytochrome p45011beta monooxygenase system. J Biol Chem, 1998. 273(37): p. 23984-92.

Lathe R. et al., Plasmid and bacteriophage vectors for excision of intact inserts. Gene, 1987. 57: p. 193-201.

Lecain E. et al., Cloning by metabolic interference in yeast and enzymatic characterization of *Arabidopsis thaliana* sterol delta 7-reductase. J Biol Chem, 1996. 271(18): p. 10866-73.

Meng-Chun Hu and Bon-chu Chung. Expression of human 21-hydroxylase (P450c21) in bacterial and mammalian cells: A system to characterize normal and mutant enzyme. DNA and Cell Biology. 1991. 10(3): p. 201-209.

Nacken, V., T. Achstetter and E. Degryse, Probing the limits of expression levels by varying promoter strength and plasmid copy number in *Saccharomyces cerevisiae*. Gene, 1996. 175(1-2): p. 253-60.

Parent S A., et al., Vector systems for the expression, analysis and cloning of DNA sequences in *S. cerevisiae*. Yeast, 1985. 1(2): p. 83-138.

Risenberg-D. and R. Guthke, High-cell-density cultivation of microorganisms. Appl. Microbiol Biotechnol, 1999. 51: p. 422-430.

Thierry et al. The complete sequence of the 8.2 kb segment left of MAT on chromosome III reveals five ORFs, including a gene for a yeast ribokinase. Yeast, 1990. Nov-Dec; 6(6): p. 521-34.

Urban, P., et al., Characterization of recombinant plant cinnamate 4-hydroxylase produced in yeast. Kinetic and spectral properties. of the major plant P450 of the phenylpropanoid pathway. Eur J Biochem, 1994. 222(3): p. 843-50.

Valvo, L., et al., General high-performance liquid chromatographic procedures for the rapid screening of natural and synthetic corticosteroids. J Pharm Biomed Anal, 1994. 12(6): p. 805-10.

Wu, DA. et al., Expression and functional study of wild-type and mutant human cytochrome P450c21 in *Saccharomyces cerevisiae*. DNA Cell Biol, 1991. 10(3): p. 201-9.

Yanisch-Perron et al., Improved M13 phage cloning vectors and host strains: nucleotide sequences of the M13 mp18 and pUC19 vectors. Gene, 1985. 33(1): p. 103-19.

Zhao H F. et al., Molecular cloning, cDNA structure and predicted amino acid sequence of bovine 3 beta-hydroxy-5-ene steroid dehydrogenase/delta 5-delta 4 isomerase. FEBS Lett, 1989. 259(1): p. 153-7.

The invention claimed is:

1. A *Saccharomyces cerevisiae* yeast strain genetically modified to autonomously produce, from a simple carbon source, a steroid or steroid derivative derived from cholesterol metabolism, wherein said steroid or steroid derivative is selected from the group consisting of pregnenolone, 17α-hydroxypregnenolone, cortisol, cortexolone, progesterone, 17α-hydroxyprogesterone, and derivatives thereof; wherein the genetic modification comprises:
   a) the inactivation of ATF2, GCY1 and YPR1, and
   b) at least one heterologous gene or cDNA in an expression cassette, wherein the gene or cDNA is selected from the group consisting of the gene or cDNA encoding *A. thaliana* sterol Δ7-reductase, bovine cytochrome $P450_{SCC}$, bovine adrenodoxin, bovine adrenodoxin reductase, bovine 3β-hydroxysteroid dehydrogenase/isomerase, human 3β-hydroxysteroid dehydrogenase/isomerase, bovine cytochrome P450 C17, human cytochrome P450 C21, human cytochrome P450 C11, bovine cytochrome P450 C11 and human-bovine hybrid cytochrome P450 C11.

2. The yeast strain of claim 1, wherein said expression cassette is located on a multicopy plasmid or a low copy plasmid.

3. The yeast strain of claim 2, wherein the expression cassette is located on multicopy plasmid, wherein said multicopy plasmid is a yeast 2-micron replicon-based plasmid which replicates in *Saccharomyces cerevisiae*, or a low copy plasmid comprising a chromosomal ARS origin of replication with a yeast centromere.

4. The yeast strain of claim 1, wherein the at least one heterologous gene or cDNA in an expression cassette is under the control of a promoter selected from the group consisting of the endogenous *S. cerevisiae* promoters TDH3, TEF1, PGK1, CYC1, GAL10, ATF2, TIR1, ARH1, ADE2, and the hybrid promoter GAL10-CYC1.

5. The yeast strain of claim 4, wherein the at least one heterologous gene or cDNA in an expression cassette comprises an operable terminator sequence selected from the group consisting of terminator sequences of the *S. cerevisiae* endogenous genes PGK1, CYC1, ATF2, ADE2 and NCP1.

6. The yeast strain of claim 1, wherein the at least one heterologous gene or cDNA in an expression cassette comprises an operable terminator sequence selected from the group consisting of terminator sequences of the *S. cerevisiae* endogenous genes PGK1, CYC1, ATF2, ADE2 and NCP1.

7. The yeast strain of claim 1, wherein the bovine cytochrome $P450_{SCC}$ is the mature form of bovine cytochrome $P450_{SCC}$ having a methionine at the $NH_2$-terminal end, and wherein the bovine adrenodoxin is the mature form of bovine adrenodoxin having a methionine at the $NH_2$-terminal end.

8. The yeast strain of claim 1, wherein the expression cassette comprises a gene or cDNA encoding bovine adrenodoxin reductase, wherein the cassette is located on a single copy plasmid, a low copy plasmid, or integrated into the yeast strain chromosome.

9. The yeast strain of claim 8, wherein the expression cassette comprises elements for ensuring that the adrenodoxin reductase is present in the cytosol of the yeast strain.

10. The yeast strain of claim 1, wherein the heterologous gene or cDNA is selected from the group consisting of the gene or cDNA encoding bovine 3β-hydroxysteroid dehydrogenase/isomerase, human 3β-hydroxysteroid dehydrogenase/isomerase, bovine cytochrome P450 C17, human cytochrome P450 C11, bovine cytochrome P450 C11 and human-bovine hybrid cytochrome P450 C11 wherein the expression cassette is located on a high copy plasmid.

11. The yeast strain of claim 1, wherein the heterologous gene or cDNA is selected from the group consisting of the gene or cDNA encoding human cytochrome P450 C11, bovine cytochrome P450 C11 and human-bovine hybrid cytochrome P450 C11, wherein the expression cassette is located on a multicopy plasmid and the cytochrome P450 C11 produced from the expression cassette comprises a signal for exporting the cytochrome P450 C11 to mitochondria.

12. The yeast strain of claim 1, wherein the yeast strain comprises at least one expression cassette encoding bovine adrenodoxin, wherein the expression cassette is located on a multicopy plasmid with a weak promoter and the adrenodoxin produced from the expression cassette comprises a signal for exporting the adrenodoxin to mitochondria.

13. The yeast strain of claim 1, wherein the yeast strain comprises at least two expression cassettes each comprising a gene or cDNA encoding bovine adrenodoxin protein, wherein said first expression cassette encodes bovine adrenodoxin protein which is active in the cytosol of said yeast strain and said second expression cassette encodes bovine adrenodoxin protein which is active in the mitochondria of the yeast strain.

14. The yeast strain of claim 1, wherein the yeast strain further comprises at least one expression cassette comprising one or more genes encoding proteins having NADPH P450 reductase activity, wherein the expression cassette is located on a single copy plasmid or integrated into the chromosome.

15. The yeast strain of claim 1, wherein said yeast strain expresses the endogenous *S. cerevisiae* ARH 1 protein at a level higher than the corresponding *S. cerevisiae* prior to being genetically modified.

16. The yeast strain of claim 15, wherein said yeast strain comprises a functional endogenous ARH1 gene and has been genetically modified by the introduction of an additional copy of the endogenous ARH1 gene or cDNA that encodes a functional ARH1 protein in an expression cassette.

17. The yeast strain of claim 16, wherein the expression of the additional endogenous ARH1 gene or cDNA is placed under the control of a CYC1 promoter.

18. A yeast strain which is the TGY260 strain deposited with the CNCM on Jan. 24, 2001 under the accession number I-2615 which further comprises an additional disruption or inactivation of the ATF2 gene.

19. The yeast strain of claim 1, comprising the genetic elements required for excreting the steroid or steroid derivative produced into the culture medium.

20. A *Saccharomyces cerevisiae* yeast strain genetically modified to autonomously produce, from a simple carbon source, a steroid or steroid derivative derived from cholesterol metabolism, wherein said steroid or steroid derivative is selected from the group consisting of pregnenolone, 17α-hydroxypregnenolone, cortisol, cortexolone, progesterone, 17α-hydroxyprogesterone, and derivatives thereof; wherein the genetic modification comprises:
   a) the inactivation of ADE2, ATF2, GCY1 and YPR1, and
   b) at least one heterologous gene or cDNA in an expression cassette, wherein the gene or cDNA is selected from the group consisting of the gene or cDNA encoding *A. thaliana* sterol Δ7-reductase, bovine cytochrome $P450_{SCC}$, bovine adrenodoxin, bovine adrenodoxin reductase, bovine 3β-hydroxysteroid dehydrogenase/isomerase, human 3β-hydroxysteroid dehydrogenase/isomerase, bovine cytochrome P450 C17, human cytochrome P450 C21, human cytochrome P450 C11, bovine cytochrome P450 C11 and human-bovine hybrid cytochrome P450 C11.

21. The yeast strain of claim 20 comprising a gene or cDNA encoding *A. thaliana* sterol Δ7-reductase in an expression cassette integrated in the yeast strain chromosome at the ADE2 locus.

22. A *Saccharomyces cerevisiae* yeast strain genetically modified to autonomously produce, from a simple carbon source, a steroid or steroid derivative derived from cholesterol metabolism, wherein said steroid or steroid derivative is selected from the group consisting of pregnenolone, 17α-hydroxypregnenolone, cortisol, cortexolone, progesterone, 17α-hydroxyprogesterone, and derivatives thereof; wherein the genetic modification comprises:
 a) the inactivation of ERG5, ATF2, GCY1 and YPR1, and
 b) at least one heterologous gene or cDNA in an expression cassette, wherein the gene or cDNA is selected from the group consisting of the gene or cDNA encoding *A. thaliana* sterol Δ7-reductase, bovine cytochrome $P450_{SCC}$, bovine adrenodoxin, bovine adrenodoxin reductase, bovine 3β-hydroxysteroid dehydrogenase/isomerase, human 3β-hydroxysteroid dehydrogenase/isomerase, bovine cytochrome P450 C17, human cytochrome P450 C21, human cytochrome P450 C11, bovine cytochrome P450 C11 and human-bovine hybrid cytochrome P450 C11.

23. A *Saccharomyces cerevisiae* yeast strain genetically modified to autonomously produce, from a simple carbon source, a steroid or steroid derivative derived from cholesterol metabolism, wherein said steroid or steroid derivative is selected from the group consisting of pregnenolone, 17α-hydroxypregnenolone, cortisol, cortexolone, progesterone, 17α-hydroxyprogesterone, and derivatives thereof; wherein the genetic modification comprises:
 a) the inactivation of ADE2, ERG5, ATF2, GCY1 and YPR1, and
 b) at least one heterologous gene or cDNA in an expression cassette, wherein the gene or cDNA is selected from the group consisting of the gene or cDNA encoding *A. thaliana* sterol Δ7-reductase, bovine cytochrome $P450_{SCC}$, bovine adrenodoxin, bovine adrenodoxin reductase, bovine 3β-hydroxysteroid dehydrogenase/isomerase, human 3β-hydroxysteroid dehydrogenase/isomerase, bovine cytochrome P450 C17, human cytochrome P450 C21, human cytochrome P450 C11, bovine cytochrome P450 C11 and human-bovine hybrid cytochrome P450 C11.

* * * * *

UNITED STATES PATENT AND TRADEMARK OFFICE
CERTIFICATE OF CORRECTION

PATENT NO.       : 7,670,829 B2
APPLICATION NO.  : 10/470673
DATED            : March 2, 2010
INVENTOR(S)      : Roberto Spagnoli et al.

It is certified that error appears in the above-identified patent and that said Letters Patent is hereby corrected as shown below:

Title Page, Item (56) On page 2, in column 1, under "Other Publications", line 16, delete "1990)" and insert -- (1990) --, therefor.

Title Page, Item (56) On page 2, in column 1, under "Other Publications", line 22, delete "Adrendoxin" and insert -- Adrenodoxin --, therefor.

Title Page, Item (56) On page 2, in column 1, under "Other Publications", line 24, delete "(1993)" and insert -- (1998) --, therefor.

Title Page, Item (56) On page 2, in column 1, under "Other Publications", line 36, delete "125" and insert -- 175 --, therefor.

Title Page, Item (56) On page 2, in column 1, under "Other Publications", line 37, delete "Parent Stephan" and insert -- Parent Stephen --, therefor.

Title Page, Item (56) On page 2, in column 1, under "Other Publications", line 43, delete "cervisiae" and insert -- cerevisiae --, therefor.

Title Page, Item (56) On page 2, in column 1, under "Other Publications", line 65, delete "Esterificatio" and insert -- Esterification --, therefor.

Title Page, Item (56) On page 2, in column 2, under "Other Publications", line 6, delete "Multiny" and insert -- Multiply --, therefor.

Title Page, Item (56) On page 2, in column 2, under "Other Publications", line 9, delete "1980" and insert -- 1990 --, therefor.

Title Page, Item (56) On page 2, in column 2, under "Other Publications", line 11, delete "Lipis," and insert -- Lipids, --, therefor.

Title Page, Item (56) On page 2, in column 2, under "Other Publications", line 13, delete "phosphte" and insert -- phosphate --, therefor.

Signed and Sealed this
Twenty-fifth Day of January, 2011

David J. Kappos
*Director of the United States Patent and Trademark Office*

Title Page, Item (56) On page 2, in column 2, under "Other Publications", line 16, delete "Saccaromyces" and insert -- Saccharomyces --, therefor.

Title Page, Item (56) On page 2, in column 2, under "Other Publications", line 19, delete "Saccharcymces" and insert -- Saccharomyces --, therefor.

Title Page, Item (56) On page 2, in column 2, under "Other Publications", line 19, after "1993," insert -- Vol. 21 --.

Title Page, Item (56) On page 2, in column 2, under "Other Publications", line 21, delete "Amphotencin" and insert -- Amphotericin --, therefor.

Title Page, Item (56) On page 2, in column 2, under "Other Publications", line 30, delete "Bio." and insert -- Biol. --, therefor.

Title Page, Item (56) On page 2, in column 2, under "Other Publications", line 33, delete "cerevisias" and insert -- cerevisiae --, therefor.

Title Page, Item (56) On page 2, in column 2, under "Other Publications", line 38, delete "Sacharomyces" and insert -- Saccharomyces --, therefor.

Title Page, Item (56) On page 2, in column 2, under "Other Publications", line 47, delete "Heterozygoet" and insert -- Heterozygote --, therefor.

Title Page, Item (56) On page 2, in column 2, under "Other Publications", line 54, delete "biphysica" and insert -- Biophysica --, therefor.

Title Page, Item (56) On page 2, in column 2, under "Other Publications", line 61, delete "Sacharomyces" and insert -- Saccharomyces --, therefor.

Title Page, Item (56) On page 2, in column 2, under "Other Publications", line 64, delete "protien" and insert -- protein --, therefor.

Title Page, Item (56) On page 2, in column 2, under "Other Publications", line 67, delete "Moelcular" and insert -- Molecular --, therefor.

Title Page, Item (56) On page 2, in column 2, under "Other Publications", line 70, delete "Cimpletionof" and insert -- Complementation of --, therefor.

Title Page, Item (56) On page 2, in column 2, under "Other Publications", line 70, delete "Saccharomyes" and insert -- Saccharomyces --, therefor.

Title Page, Item (56) On page 2, in column 2, under "Other Publications", line 70, delete "crevisiae autotrophic" and insert -- cerevisiae auxotrophic --, therefor.

Title Page, Item (56) On page 3, in column 1, under "Other Publications", line 7, delete "Galor" and insert -- Galore --, therefor.

Title Page, Item (56) On page 3, in column 1, under "Other Publications", line 8, delete "form" and insert -- from --, therefor.

Title Page, Item (56) On page 3, in column 1, under "Other Publications", line 12, delete "Sacharomyces" and insert -- Saccharomyces --, therefor.

Title Page, Item (56) On page 3, in column 1, under "Other Publications", line 12, delete "1,4" and insert -- 1.4M NaCl --, therefor.

Title Page, Item (56) On page 3, in column 1, under "Other Publications", line 15, delete "toa" and insert -- to a --, therefor.

Title Page, Item (56) On page 3, in column 1, under "Other Publications", line 20, after "of" insert -- a --.

Title Page, Item (56) On page 3, in column 1, under "Other Publications", line 23, delete "Exprssion" and insert -- Expression --, therefor.

Title Page, Item (56) On page 3, in column 1, under "Other Publications", line 25, delete "No. 9" and insert -- No. 8 --, therefor.

Title Page, Item (56) On page 3, in column 1, under "Other Publications", line 30, delete "P50c17" and insert -- P450c17 --, therefor.

Title Page, Item (56) On page 3, in column 1, under "Other Publications", line 32, delete "Pharmacogenstics" and insert -- Pharmacogenetics --, therefor.

Title Page, Item (56) On page 3, in column 1, under "Other Publications", line 37, delete "cerevisias" and insert -- cerevisiae --, therefor.

Title Page, Item (56) On page 3, in column 1, under "Other Publications", line 37, delete "241" and insert -- 240 --, therefor.

Title Page, Item (56) On page 3, in column 1, under "Other Publications", line 40, delete "Biochimia" and insert -- Biochim Biophys Acta --, therefor.

Title Page, Item (56) On page 3, in column 2, under "Other Publications", line 3, delete "Cylochrome" and insert -- Cytochrome --, therefor.

Title Page, Item (56) On page 3, in column 2, under "Other Publications", line 4, delete "19176-19196" and insert -- 19176-19186--, therefor.

CERTIFICATE OF CORRECTION (continued)

U.S. Pat. No. 7,670,829 B2

Title Page, Item (56) On page 3, in column 2, under "Other Publications", line 9, delete "ceevisiae" and insert -- cerevisiae --, therefor.

Title Page, Item (56) On page 3, in column 2, under "Other Publications", line 11, delete "Characterizaiton" and insert -- Characterization --, therefor.

Title Page, Item (56) On page 3, in column 2, under "Other Publications", line 15, delete "Limil" and insert -- Smith-Lemli-Optiz syndrome --, therefor.

Title Page, Item (56) On page 3, in column 2, under "Other Publications", line 19, delete "Europeon" and insert -- European --, therefor.

Title Page, Item (56) On page 3, in column 2, under "Other Publications", line 31, delete "Hydorxylse" and insert -- Hydroxylase --, therefor.

Title Page, Item (56) On page 3, in column 2, under "Other Publications", line 37, delete "Chapter 6" and insert -- Chapter 5 --, therefor.

In column 6, line 41, delete "genes-are" and insert -- genes are --, therefor.

In column 7, line 47, delete "since is appears" and insert -- since it appears --, therefor.

In column 8, line 37, delete "percursors" and insert -- precursors --, therefor.

In column 10, line 11, delete "leu2 $\Delta$1" and insert -- leu2$\Delta$1 --, therefor.

In column 10, line 13, delete "the" and insert -- -the --, therefor.

In column 10, line 14, delete "leu2 $\Delta$1" and insert -- leu2$\Delta$1 --, therefor.

In column 10, line 67, delete "PCR5" and insert -- PCRs --, therefor.

In column 11, line 1, delete "PCR5" and insert -- PCRs --, therefor.

In column 11, line 52, delete "trytophan" and insert -- tryptophan --, therefor.

In column 13, line 15, delete "plamid" and insert -- plasmid --, therefor.

In column 13, line 21, delete "BamH1" and insert -- BamHI --, therefor.

In column 13, line 67, delete "PCR5" and insert -- PCRs --, therefor.

In column 14, line 19-20, delete "30 s" and insert -- 30s --, therefor.

CERTIFICATE OF CORRECTION (continued)
U.S. Pat. No. 7,670,829 B2

In column 18, line 7, delete "GAAAPKAVLPEAMP" and insert -- GAAAPKAVLPFEAMP --, therefor.

In column 18, line 17, delete "P450111" and insert -- P45011β1 --, therefor.

In column 18, line 45, delete "a for" and insert -- for a --, therefor.

In column 18, line 46, delete "mitochrondria" and insert -- mitochondria --, therefor.

In column 21, line 22, delete "MuII" and insert -- MIuI --, therefor.

In column 22, line 1, delete "EcoRI" and insert -- EcoR1 --, therefor.

In column 22, line 10, delete "-containing" and insert -- containing --, therefor.

In column 24, line 62, delete "17OH-progesterone" and insert -- 17OH-progesterone --, therefor.

In column 24, line 65, delete "17αH-progesterone" and insert -- 17OH-progesterone --, therefor.

In column 24, line 67, delete "1-deoxycortisol." and insert -- 11-deoxycortisol. --, therefor.

In column 26, line 7, delete "nucelotides" and insert -- nucleotides --, therefor.

In column 28, line 33, delete "$P450_{11\beta}$" and insert -- P45011β --, therefor.

In column 31, line 61, delete "fens" and insert --$fen^s$--, therefor.

In column 31, line 62, delete "Fy679" and insert -- Fy1679 --, therefor.

In column 32, line 5, delete "MATαade2" and insert -- MATα ade2 -- therefor.

In column 32, line 14, delete "MATαade2" and insert -- MATα ade2 --, therefor.

In column 32, line 26, delete "MATa" and insert -- MATα --, therefor.

In column 32, line 26, delete ""A7" and insert -- Δ7 --, therefor.

In column 32, line 36, delete "UCY26¯" and insert -- UCY26 --, therefor.

In column 32, line 36, delete "G418R" and insert -- $G418^R$ --, therefor.

In column 32, line 47, delete "G418R" and insert -- $G418^R$ --, therefor.

In column 32, line 49, delete "G418R" and insert -- $G418^R$ --, therefor...

CERTIFICATE OF CORRECTION (continued)
U.S. Pat. No. 7,670,829 B2

In column 32, line 51, delete "G418R" and insert -- $G418^R$ --, therefor.

In column 32, line 61, delete "Kappeli C J," and insert -- Kappeli O J, --, therefor.

In column 32, line 67, after "609-15" insert -- . --.

In column 34, line 27, delete "properties." and insert -- properties --, therefor.

In column 34, line 37, delete "M13 mp18" and insert -- M13mp18 --, therefor.

In column 52, line 6-7, in claim 11, delete "P450 C11produced" and insert -- P450 C11 produced --, therefor.

In column 52, line 29, in claim 15, delete "ARH 1" and insert -- ARH1 --, therefor.